US011504140B2

(12) United States Patent
Fallin et al.

(10) Patent No.: US 11,504,140 B2
(45) Date of Patent: Nov. 22, 2022

(54) TRANSOSSEOUS GUIDE AND METHOD

(71) Applicant: Crossroads Extremity Systems, LLC, Memphis, TN (US)

(72) Inventors: T. Wade Fallin, Hyde Park, UT (US); Joel Helgerson, Erie, CO (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 1 day.

(21) Appl. No.: 17/068,909

(22) Filed: Oct. 13, 2020

(65) Prior Publication Data

US 2021/0022755 A1 Jan. 28, 2021

Related U.S. Application Data

(60) Division of application No. 15/887,095, filed on Feb. 2, 2018, now Pat. No. 10,820,918, which is a continuation-in-part of application No. 15/211,764, filed on Jul. 15, 2016, now Pat. No. 10,258,401, and a continuation-in-part of application No. 15/211,673, filed on Jul. 15, 2016, now Pat. No. 10,154,868.

(60) Provisional application No. 62/193,888, filed on Jul. 17, 2015.

(51) Int. Cl.
| | |
|---|---|
| *A61B 17/17* | (2006.01) |
| *A61B 17/04* | (2006.01) |
| *A61B 17/88* | (2006.01) |
| *A61B 17/16* | (2006.01) |

(52) U.S. Cl.
CPC ...... *A61B 17/1796* (2013.01); *A61B 17/0469* (2013.01); *A61B 17/0482* (2013.01); *A61B 17/1697* (2013.01); *A61B 17/1714* (2013.01); *A61B 17/1778* (2016.11); *A61B 17/8861* (2013.01); *A61B 17/0401* (2013.01); *A61B 17/0485* (2013.01)

(58) Field of Classification Search
CPC ............ A61B 17/1778; A61B 17/1796; A61B 17/0469; A61B 17/0482; A61B 17/1697; A61B 17/1714; A61B 17/8861
See application file for complete search history.

(56) References Cited

U.S. PATENT DOCUMENTS

| | | |
|---|---|---|
| 1,583,271 A | 5/1926 | Biro |
| 1,586,721 A | 6/1926 | Tryon |
| 1,856,721 A | 5/1932 | Nagelmann |
| 2,291,413 A | 7/1942 | Siebrandt |
| 4,312,337 A | 1/1982 | Donohue |

(Continued)

FOREIGN PATENT DOCUMENTS

| | | |
|---|---|---|
| WO | 95/15726 A1 | 6/1995 |
| WO | 98/06344 A1 | 2/1998 |

(Continued)

OTHER PUBLICATIONS 2.5 mm PushLock Knotless Suture Anchor, Arthrex, Inc., www.arthrex.com, 2013, 2 pp.

(Continued)

*Primary Examiner* — Tessa M Matthews
(74) *Attorney, Agent, or Firm* — BakerHostetler

(57) ABSTRACT

Instruments and methods for surgical transosseous attachment to a bone include a guide able to guide the formation of intersecting bone tunnels and a passer able to pass a member through the bone tunnels.

10 Claims, 29 Drawing Sheets

(56) References Cited

U.S. PATENT DOCUMENTS

| | | |
|---|---|---|
| 4,441,497 A | 4/1984 | Paudler |
| 4,622,960 A | 11/1986 | Tam |
| 4,672,957 A | 6/1987 | Hourahane |
| 4,738,255 A | 4/1988 | Goble et al. |
| 4,741,330 A | 5/1988 | Hayhurst |
| 4,784,126 A | 11/1988 | Hourahane |
| 4,809,408 A | 3/1989 | Abrahamson |
| 4,890,615 A | 1/1990 | Caspari et al. |
| 4,898,156 A | 2/1990 | Gatturna et al. |
| 4,959,069 A | 9/1990 | Brennan et al. |
| 5,037,422 A | 8/1991 | Hayhurst et al. |
| 5,041,129 A | 8/1991 | Hayhurst et al. |
| 5,100,417 A | 3/1992 | Cerier et al. |
| 5,176,682 A | 1/1993 | Chow |
| 5,224,946 A | 7/1993 | Hayhurst et al. |
| 5,236,445 A | 8/1993 | Hayhurst et al. |
| 5,250,055 A | 10/1993 | Moore et al. |
| 5,254,126 A | 10/1993 | Filipi et al. |
| 5,257,996 A | 11/1993 | McGuire |
| 5,258,016 A | 11/1993 | Dipoto et al. |
| 5,268,001 A | 12/1993 | Nicholson et al. |
| 5,269,809 A | 12/1993 | Hayhurst et al. |
| 5,312,438 A | 5/1994 | Johnson |
| 5,330,468 A | 7/1994 | Burkhart |
| 5,336,240 A | 8/1994 | Metzler et al. |
| 5,342,369 A | 8/1994 | Harryman, II |
| 5,350,380 A | 9/1994 | Goble et al. |
| 5,354,300 A | 10/1994 | Goble et al. |
| 5,411,523 A | 5/1995 | Goble |
| 5,417,691 A | 5/1995 | Hayhurst |
| 5,417,701 A | 5/1995 | Holmes |
| 5,439,467 A | 8/1995 | Benderev et al. |
| 5,454,823 A | 10/1995 | Richardson et al. |
| 5,464,427 A | 11/1995 | Curtis et al. |
| 5,466,243 A | 11/1995 | Schmieding et al. |
| 5,480,403 A | 1/1996 | Lee et al. |
| 5,486,197 A | 1/1996 | Le et al. |
| 5,544,664 A | 8/1996 | Benderev et al. |
| 5,545,180 A | 8/1996 | Le et al. |
| 5,562,683 A | 10/1996 | Chan |
| 5,562,684 A | 10/1996 | Kammerer |
| 5,562,687 A | 10/1996 | Chan |
| 5,569,306 A | 10/1996 | Thal |
| 5,572,770 A | 11/1996 | Boden |
| 5,575,801 A | 11/1996 | Habermeyer et al. |
| 5,584,836 A | 12/1996 | Ballintyn et al. |
| 5,584,839 A | 12/1996 | Gieringer |
| 5,601,557 A | 2/1997 | Hayhurst |
| 5,601,562 A | 2/1997 | Wolf et al. |
| 5,620,012 A | 4/1997 | Benderev et al. |
| 5,624,446 A | 4/1997 | Harryman, II |
| 5,630,824 A | 5/1997 | Hart |
| 5,637,112 A | 6/1997 | Moore et al. |
| 5,643,321 A | 7/1997 | McDevitt |
| 5,645,568 A | 7/1997 | Chervitz et al. |
| 5,647,874 A | 7/1997 | Hayhurst |
| 5,649,963 A | 7/1997 | McDevitt |
| 5,658,313 A | 8/1997 | Thal |
| 5,665,112 A | 9/1997 | Thal |
| 5,681,333 A | 10/1997 | Burkhart et al. |
| 5,683,401 A | 11/1997 | Schmieding et al. |
| 5,683,418 A | 11/1997 | Luscombe et al. |
| 5,683,419 A | 11/1997 | Thal |
| 5,688,284 A | 11/1997 | Chervitz et al. |
| 5,690,676 A | 11/1997 | Dipoto et al. |
| 5,690,677 A | 11/1997 | Schmieding et al. |
| 5,700,266 A | 12/1997 | Harryman, II |
| 5,702,397 A | 12/1997 | Goble et al. |
| 5,702,398 A | 12/1997 | Tarabishy |
| 5,709,708 A | 1/1998 | Thal |
| 5,720,765 A | 2/1998 | Thal |
| 5,725,529 A | 3/1998 | Nicholson et al. |
| 5,728,136 A | 3/1998 | Thal |
| 5,730,747 A | 3/1998 | Ek et al. |
| 5,733,307 A | 3/1998 | Dinsdale |
| 5,746,754 A | 5/1998 | Chan |
| 5,746,763 A | 5/1998 | Benderev et al. |
| 5,749,884 A | 5/1998 | Benderev et al. |
| 5,755,728 A | 5/1998 | Maki |
| 5,766,221 A | 6/1998 | Benderev et al. |
| 5,776,151 A | 7/1998 | Chan |
| 5,782,864 A | 7/1998 | Lizardi |
| 5,797,963 A | 8/1998 | McDevitt |
| 5,800,447 A | 9/1998 | Wenstrom, Jr. |
| 5,814,071 A | 9/1998 | McDevitt et al. |
| 5,824,009 A | 10/1998 | Fukuda et al. |
| RE36,020 E | 12/1998 | Moore et al. |
| 5,842,478 A | 12/1998 | Benderev et al. |
| 5,860,978 A | 1/1999 | McDevitt et al. |
| 5,868,762 A | 2/1999 | Cragg et al. |
| 5,891,150 A | 4/1999 | Chan |
| 5,891,168 A | 4/1999 | Thal |
| 5,895,425 A | 4/1999 | Grafton et al. |
| 5,906,624 A | 5/1999 | Wenstrom, Jr. |
| 5,911,721 A | 6/1999 | Nicholson et al. |
| 5,918,604 A | 7/1999 | Whelan |
| 5,935,129 A | 8/1999 | McDevitt et al. |
| 5,938,686 A | 8/1999 | Benderev et al. |
| 5,947,982 A | 9/1999 | Duran |
| 5,948,000 A | 9/1999 | Larsen et al. |
| 5,957,924 A | 9/1999 | Toermaelae et al. |
| 5,961,530 A | 10/1999 | Moore et al. |
| 5,964,783 A | 10/1999 | Grafton et al. |
| 5,968,044 A | 10/1999 | Nicholson et al. |
| 5,980,558 A | 11/1999 | Wiley |
| 6,001,104 A | 12/1999 | Benderev et al. |
| 6,024,758 A | 2/2000 | Thal |
| 6,029,805 A | 2/2000 | Alpern et al. |
| 6,045,574 A | 4/2000 | Thal |
| 6,086,608 A | 7/2000 | Ek et al. |
| 6,099,538 A | 8/2000 | Moses et al. |
| 6,120,511 A | 9/2000 | Chan |
| 6,132,433 A | 10/2000 | Whelan |
| 6,143,017 A | 11/2000 | Thal |
| 6,156,039 A | 12/2000 | Thal |
| 6,183,479 B1 | 2/2001 | Toermaelae et al. |
| 6,267,766 B1 | 7/2001 | Burkhart |
| 6,290,711 B1 | 9/2001 | Caspari et al. |
| 6,302,886 B1 | 10/2001 | McDevitt et al. |
| 6,319,252 B1 | 11/2001 | McDevitt et al. |
| 6,319,269 B1 | 11/2001 | Li |
| 6,368,335 B1 | 4/2002 | Chan |
| 6,371,124 B1 | 4/2002 | Whelan |
| 6,387,129 B2 | 5/2002 | Rieser et al. |
| RE37,963 E | 1/2003 | Thal |
| 6,508,830 B2 | 1/2003 | Steiner |
| 6,511,487 B1 | 1/2003 | Oren et al. |
| 6,514,274 B1 | 2/2003 | Boucher et al. |
| 6,517,546 B2 | 2/2003 | Whittaker et al. |
| 6,520,980 B1 | 2/2003 | Foerster |
| 6,524,316 B1 | 2/2003 | Nicholson et al. |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,537,319 B2 | 3/2003 | Whelan |
| 6,540,750 B2 | 4/2003 | Burkhart |
| 6,544,281 B2 | 4/2003 | Elattrache et al. |
| 6,547,807 B2 | 4/2003 | Chan et al. |
| 6,585,730 B1 | 7/2003 | Foerster |
| 6,599,295 B1 | 7/2003 | Tornier et al. |
| 6,605,096 B1 | 8/2003 | Ritchart |
| 6,610,064 B1 | 8/2003 | Goble et al. |
| 6,616,674 B2 | 9/2003 | Schmieding |
| 6,623,524 B2 | 9/2003 | Schmieding |
| 6,629,984 B1 | 10/2003 | Chan |
| 6,638,283 B2 | 10/2003 | Thal |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,561 B1 | 11/2003 | Tran |
| 6,656,182 B1 | 12/2003 | Hayhurst |
| 6,656,183 B2 | 12/2003 | Colleran et al. |
| 6,660,023 B2 | 12/2003 | McDevitt et al. |
| 6,673,094 B1 | 1/2004 | McDevitt et al. |

(56) References Cited

U.S. PATENT DOCUMENTS

| | | |
|---|---|---|
| 6,692,516 B2 | 2/2004 | West et al. |
| 6,712,849 B2 | 3/2004 | Re et al. |
| 6,716,234 B2 | 4/2004 | Grafton et al. |
| 6,723,107 B1 | 4/2004 | Skiba et al. |
| 6,733,506 B1 | 5/2004 | McDevitt et al. |
| 6,733,529 B2 | 5/2004 | Whelan |
| 6,743,233 B1 | 6/2004 | Baldwin et al. |
| 6,770,073 B2 | 8/2004 | McDevitt et al. |
| 6,770,076 B2 | 8/2004 | Foerster |
| 6,770,084 B1 | 8/2004 | Bain et al. |
| 6,780,198 B1 | 8/2004 | Gregoire et al. |
| 6,830,572 B2 | 12/2004 | McDevitt et al. |
| 6,855,157 B2 | 2/2005 | Foerster et al. |
| 6,860,887 B1 | 3/2005 | Frankle |
| 6,878,166 B2 | 4/2005 | Clark et al. |
| 6,887,259 B2 | 5/2005 | Lizardi |
| 6,932,826 B2 | 8/2005 | Chan |
| 6,942,683 B2 | 9/2005 | Dunshee |
| 6,942,684 B2 | 9/2005 | Bonutti |
| 6,955,678 B2 | 10/2005 | Gabriel et al. |
| 6,958,067 B2 | 10/2005 | Whittaker et al. |
| 6,974,477 B2 | 12/2005 | Whelan |
| 6,984,237 B2 | 1/2006 | Hatch et al. |
| 6,986,781 B2 | 1/2006 | Smith |
| 6,991,636 B2 | 1/2006 | Rose |
| 6,994,719 B2 | 2/2006 | Grafton |
| 6,994,725 B1 | 2/2006 | Goble |
| 7,029,490 B2 | 4/2006 | Grafton et al. |
| 7,033,364 B1 | 4/2006 | Walters et al. |
| 7,037,324 B2 | 5/2006 | Martinek |
| 7,063,724 B2 | 6/2006 | Re et al. |
| 7,066,956 B2 | 6/2006 | Schmieding et al. |
| 7,074,203 B1 | 7/2006 | Johanson et al. |
| 7,077,863 B2 | 7/2006 | Schmieding et al. |
| 7,081,126 B2 | 7/2006 | McDevitt et al. |
| 7,083,638 B2 | 8/2006 | Foerster |
| 7,108,700 B2 | 9/2006 | Chan |
| 7,112,208 B2 | 9/2006 | Morris et al. |
| 7,147,651 B2 | 12/2006 | Morrison et al. |
| 7,172,595 B1 | 2/2007 | Goble |
| 7,175,632 B2 | 2/2007 | Singhatat et al. |
| 7,195,642 B2 | 3/2007 | McKernan et al. |
| 7,201,756 B2 | 4/2007 | Ross et al. |
| 7,226,469 B2 | 6/2007 | Benavitz et al. |
| 7,229,448 B2 | 6/2007 | Goble et al. |
| 7,235,100 B2 | 6/2007 | Martinek |
| 7,247,164 B1 | 7/2007 | Ritchart et al. |
| 7,285,124 B2 | 10/2007 | Foerster |
| 7,306,626 B2 | 12/2007 | Whelan |
| 7,309,337 B2 | 12/2007 | Colleran et al. |
| 7,309,346 B2 | 12/2007 | Martinek |
| 7,329,272 B2 | 2/2008 | Burkhart et al. |
| 7,341,592 B1 | 3/2008 | Walters et al. |
| D569,973 S | 5/2008 | Oren et al. |
| 7,377,926 B2 | 5/2008 | Topper et al. |
| 7,381,212 B2 | 6/2008 | Topper et al. |
| 7,381,213 B2 | 6/2008 | Lizardi |
| 7,399,302 B2 | 7/2008 | Goble et al. |
| D576,277 S | 9/2008 | Oren et al. |
| 7,458,975 B2 | 12/2008 | May et al. |
| 7,465,308 B2 | 12/2008 | Sikora et al. |
| 7,500,990 B2 | 3/2009 | Whelan |
| 7,517,357 B2 | 4/2009 | Abrams et al. |
| 7,527,648 B2 | 5/2009 | May et al. |
| 7,530,999 B2 | 5/2009 | Clark et al. |
| 7,556,640 B2 | 7/2009 | Foerster |
| 7,569,059 B2 | 8/2009 | Cerundolo |
| 7,585,305 B2 | 9/2009 | Dreyfuss |
| 7,585,311 B2 | 9/2009 | Green et al. |
| 7,588,587 B2 | 9/2009 | Barbieri et al. |
| 7,588,595 B2 | 9/2009 | Miller et al. |
| 7,594,917 B2 | 9/2009 | Whittaker et al. |
| 7,608,084 B2 | 10/2009 | Oren et al. |
| 7,625,386 B2 | 12/2009 | Abe et al. |
| 7,637,926 B2 | 12/2009 | Foerster et al. |
| 7,651,495 B2 | 1/2010 | McDevitt et al. |
| 7,655,011 B2 | 2/2010 | Whittaker et al. |
| 7,662,171 B2 | 2/2010 | West et al. |
| 7,674,275 B2 | 3/2010 | Martin et al. |
| 7,674,290 B2 | 3/2010 | McKernan et al. |
| 7,678,134 B2 | 3/2010 | Schmieding et al. |
| 7,682,374 B2 | 3/2010 | Foerster et al. |
| 7,695,494 B2 | 4/2010 | Foerster |
| 7,713,286 B2 | 5/2010 | Singhatat |
| 7,713,300 B2 | 5/2010 | Meridew et al. |
| 7,749,237 B2 | 7/2010 | Chan |
| 7,771,441 B2 | 8/2010 | Cerundolo |
| 7,803,173 B2 | 9/2010 | Burkhart et al. |
| 7,819,898 B2 | 10/2010 | Stone et al. |
| 7,833,230 B2 | 11/2010 | Cerundolo |
| 7,833,244 B2 | 11/2010 | Cerundolo |
| 7,837,710 B2 | 11/2010 | Lombardo et al. |
| 7,837,718 B2 | 11/2010 | Clark et al. |
| 7,842,050 B2 | 11/2010 | Diduch et al. |
| 7,867,251 B2 | 1/2011 | Colleran et al. |
| 7,867,264 B2 | 1/2011 | McDevitt et al. |
| 7,868,251 B2 | 1/2011 | Gladd et al. |
| 7,879,046 B2 | 2/2011 | Weinert et al. |
| 7,879,048 B2 | 2/2011 | Bain et al. |
| 7,883,519 B2 | 2/2011 | Oren et al. |
| 7,892,256 B2 | 2/2011 | Grafton et al. |
| 7,896,907 B2 | 3/2011 | McDevitt et al. |
| 7,896,917 B2 | 3/2011 | Walters et al. |
| 7,905,903 B2 | 3/2011 | Stone et al. |
| 7,931,657 B2 | 4/2011 | Walters et al. |
| 7,938,847 B2 | 5/2011 | Fanton et al. |
| 7,942,878 B2 | 5/2011 | Fernandez |
| 7,942,914 B2 | 5/2011 | Cerundolo |
| 7,955,341 B2 | 6/2011 | Cerundolo |
| 7,959,649 B2 | 6/2011 | Burkhart |
| 7,959,650 B2 | 6/2011 | Kaiser et al. |
| 7,963,972 B2 | 6/2011 | Foerster et al. |
| 7,963,983 B2 | 6/2011 | Cerundolo |
| RE42,526 E | 7/2011 | Reiser et al. |
| 7,976,565 B1 | 7/2011 | Meridew |
| 7,981,140 B2 | 7/2011 | Burkhart |
| 7,988,697 B2 | 8/2011 | Miller et al. |
| 7,993,369 B2 | 8/2011 | Dreyfuss et al. |
| 8,012,171 B2 | 9/2011 | Schmieding |
| 8,012,172 B2 | 9/2011 | Grafton et al. |
| 8,012,174 B2 | 9/2011 | Elattrache et al. |
| 8,029,537 B2 | 10/2011 | West et al. |
| 8,038,652 B2 | 10/2011 | Morrison et al. |
| 8,043,308 B2 | 10/2011 | Bittenson |
| 8,062,295 B2 | 11/2011 | McDevitt et al. |
| 8,080,013 B2 | 12/2011 | Whittaker et al. |
| 8,083,769 B2 | 12/2011 | Cauldwell et al. |
| 8,088,146 B2 | 1/2012 | Wert et al. |
| 8,100,942 B1 | 1/2012 | Green et al. |
| 8,105,343 B2 | 1/2012 | White et al. |
| 8,109,966 B2 | 2/2012 | Ritchart et al. |
| 8,109,969 B1 | 2/2012 | Green et al. |
| 8,114,128 B2 | 2/2012 | Cauldwell et al. |
| 8,118,835 B2 | 2/2012 | Weisel et al. |
| 8,128,634 B2 | 3/2012 | Whittaker et al. |
| 8,133,258 B2 | 3/2012 | Foerster et al. |
| 8,137,360 B2 | 3/2012 | Whittaker et al. |
| 8,137,381 B2 | 3/2012 | Foerster et al. |
| 8,137,383 B2 | 3/2012 | West et al. |
| 8,147,505 B2 | 4/2012 | Delli-Santi |
| 8,162,978 B2 | 4/2012 | Lombardo et al. |
| 8,167,906 B2 | 5/2012 | Cauldwell et al. |
| 8,177,796 B2 | 5/2012 | Akyuz et al. |
| 8,202,295 B2 | 6/2012 | Kaplan |
| 8,202,296 B2 | 6/2012 | Burkhart |
| 8,202,297 B2 | 6/2012 | Burkhart |
| 8,226,716 B2 | 7/2012 | McKernan et al. |
| 8,231,653 B2 | 7/2012 | Dreyfuss |
| 8,262,675 B2 | 9/2012 | Cropper et al. |
| 8,267,964 B2 | 9/2012 | Green et al. |
| 8,277,451 B2 | 10/2012 | Fernandez |
| 8,277,458 B2 | 10/2012 | Schneider |
| 8,277,464 B2 | 10/2012 | Bittenson |
| 8,277,484 B2 | 10/2012 | Barbieri et al. |

(56) References Cited

U.S. PATENT DOCUMENTS

| | | |
|---|---|---|
| 8,282,643 B2 | 10/2012 | Dross |
| 8,282,659 B2 | 10/2012 | Oren et al. |
| 8,298,262 B2 | 10/2012 | Stone et al. |
| 8,317,829 B2 | 11/2012 | Foerster et al. |
| 8,317,862 B2 | 11/2012 | Troger et al. |
| 8,328,843 B2 | 12/2012 | Oren et al. |
| 8,348,975 B2 | 1/2013 | Dreyfuss |
| 8,361,079 B2 | 1/2013 | Pandya |
| 8,372,124 B2 | 2/2013 | Paulk et al. |
| 8,382,835 B2 | 2/2013 | Meridew et al. |
| 8,383,188 B2 | 2/2013 | Mazzocca et al. |
| 8,388,654 B2 | 3/2013 | Snyder et al. |
| 8,394,112 B2 | 3/2013 | Nason |
| 8,394,123 B2 | 3/2013 | Cauldwell et al. |
| 8,409,204 B2 | 4/2013 | Martin et al. |
| 8,409,225 B2 | 4/2013 | Bull et al. |
| 8,419,794 B2 | 4/2013 | Elattrache et al. |
| 8,425,536 B2 | 4/2013 | Foerster et al. |
| 8,430,909 B2 | 4/2013 | Dreyfuss et al. |
| 8,435,264 B2 | 5/2013 | Sojka et al. |
| 8,444,672 B2 | 5/2013 | Foerster |
| 8,444,674 B2 | 5/2013 | Kaplan |
| 8,449,552 B2 | 5/2013 | Sanders |
| 8,454,654 B2 | 6/2013 | Ferragamo et al. |
| 8,460,340 B2 | 6/2013 | Sojka et al. |
| 8,465,521 B2 | 6/2013 | Cook et al. |
| 8,465,522 B2 | 6/2013 | Burkhart |
| 8,469,998 B2 | 6/2013 | Sojka et al. |
| 8,475,436 B1 | 7/2013 | Jordan |
| 8,491,595 B2 | 7/2013 | Volpi et al. |
| 8,491,600 B2 | 7/2013 | McDevitt et al. |
| 8,506,596 B2 | 8/2013 | Stone et al. |
| 8,512,378 B2 | 8/2013 | Green et al. |
| 8,518,091 B2 | 8/2013 | McDevitt et al. |
| 8,523,902 B2 | 9/2013 | Heaven et al. |
| 8,529,577 B2 | 9/2013 | Hirt et al. |
| 8,529,601 B2 | 9/2013 | Green et al. |
| 8,535,350 B2 | 9/2013 | Lizardi et al. |
| 8,540,732 B2 | 9/2013 | Weinert et al. |
| 8,540,737 B2 | 9/2013 | Steven |
| 8,551,123 B2 | 10/2013 | Pandya |
| 8,556,911 B2 | 10/2013 | Mehta et al. |
| 8,579,974 B2 | 11/2013 | Pandya |
| 8,591,580 B2 | 11/2013 | McKernan et al. |
| 8,597,328 B2 | 12/2013 | Cauldwell et al. |
| 8,613,756 B2 | 12/2013 | Lizardi et al. |
| 8,617,186 B2 | 12/2013 | White et al. |
| 8,617,219 B2 | 12/2013 | Oren et al. |
| 8,623,032 B2 | 1/2014 | Diduch et al. |
| 8,652,171 B2 | 2/2014 | Stone et al. |
| 8,657,854 B2 | 2/2014 | Foerster et al. |
| 8,663,279 B2 | 3/2014 | Burkhart et al. |
| 8,663,280 B2 | 3/2014 | Kaplan |
| 8,672,954 B2 | 3/2014 | Oren et al. |
| 8,672,966 B2 | 3/2014 | Wert et al. |
| 8,672,967 B2 | 3/2014 | Dimatteo et al. |
| 8,672,970 B2 | 3/2014 | Ferragamo et al. |
| 8,685,060 B2 | 4/2014 | Foerster |
| 8,690,915 B2 | 4/2014 | Hootstein |
| 8,696,688 B2 | 4/2014 | Stone |
| 8,702,752 B2 | 4/2014 | Schmieding et al. |
| 8,702,754 B2 | 4/2014 | Dimatteo et al. |
| 8,709,040 B2 | 4/2014 | Anderhub et al. |
| 8,709,395 B2 | 4/2014 | Boutros |
| 8,721,650 B2 | 5/2014 | Fanton et al. |
| 8,740,913 B2 | 6/2014 | Schneider |
| 8,747,469 B2 | 6/2014 | Wang et al. |
| 8,764,798 B2 | 7/2014 | Housman |
| 8,771,315 B2 | 7/2014 | Lunn et al. |
| 8,771,351 B2 | 7/2014 | Elattrache et al. |
| 8,777,990 B2 | 7/2014 | Van et al. |
| 8,784,449 B2 | 7/2014 | Snyder et al. |
| 8,784,489 B2 | 7/2014 | Walters et al. |
| 8,790,370 B2 | 7/2014 | Spenciner et al. |
| 8,808,326 B2 | 8/2014 | Gagliano |
| 8,814,905 B2 | 8/2014 | Sengun et al. |
| 8,828,029 B2 | 9/2014 | White et al. |
| 8,834,495 B2 | 9/2014 | White et al. |
| 8,834,521 B2 | 9/2014 | Pinto et al. |
| 8,834,543 B2 | 9/2014 | McDevitt et al. |
| 8,858,560 B2 | 10/2014 | Bradley et al. |
| 8,870,877 B2 | 10/2014 | Koogle, Jr. |
| 8,881,635 B2 | 11/2014 | Martin |
| 8,882,801 B2 | 11/2014 | Dimatteo et al. |
| 8,906,060 B2 | 12/2014 | Hart |
| 8,926,663 B2 | 1/2015 | Green et al. |
| 8,936,620 B2 | 1/2015 | Kaiser et al. |
| 8,943,941 B2 | 2/2015 | Dow et al. |
| 8,951,292 B2 | 2/2015 | Paulk et al. |
| 8,961,576 B2 | 2/2015 | Hodge et al. |
| 8,986,345 B2 | 3/2015 | Denham et al. |
| 8,986,346 B2 | 3/2015 | Dreyfuss |
| 8,986,347 B2 | 3/2015 | Housman |
| 8,992,573 B2 | 3/2015 | Van et al. |
| 9,005,246 B2 | 4/2015 | Burkhart et al. |
| 9,017,381 B2 | 4/2015 | Kaiser et al. |
| 9,023,083 B2 | 5/2015 | Foerster et al. |
| 9,034,014 B2 | 5/2015 | Catania et al. |
| 9,044,222 B2 | 6/2015 | Dross |
| 9,044,226 B2 | 6/2015 | Green et al. |
| 9,107,653 B2 | 8/2015 | Sullivan |
| 9,113,859 B2 | 8/2015 | Dooney et al. |
| 9,144,425 B2 | 9/2015 | Kaplan |
| 9,149,268 B2 | 10/2015 | Grau et al. |
| 9,155,542 B2 | 10/2015 | Markarian |
| 9,161,750 B2 | 10/2015 | Zirps et al. |
| 9,179,907 B2 | 11/2015 | Elattrache et al. |
| 9,198,649 B2 | 12/2015 | Karapetian et al. |
| 9,226,742 B2 | 1/2016 | Wolf et al. |
| 9,265,496 B2 | 2/2016 | Sojka et al. |
| 9,307,979 B1 | 4/2016 | Bennett et al. |
| 9,445,805 B2 | 9/2016 | Snell et al. |
| 9,498,232 B2 | 11/2016 | Perez, III |
| 9,782,165 B2 | 10/2017 | Murphy et al. |
| 10,219,813 B2 | 3/2019 | Okuno et al. |
| 10,426,460 B2 | 10/2019 | Taber et al. |
| 2001/0016747 A1 | 8/2001 | Romano et al. |
| 2002/0029066 A1 | 3/2002 | Foerster |
| 2002/0065526 A1 | 5/2002 | Oren et al. |
| 2003/0105524 A1 | 6/2003 | Paulos et al. |
| 2003/0171778 A1 | 9/2003 | Lizardi |
| 2003/0195528 A1 | 10/2003 | Ritchart |
| 2003/0195563 A1 | 10/2003 | Foerster |
| 2003/0229362 A1 | 12/2003 | Chan et al. |
| 2004/0010286 A1 | 1/2004 | Gieringer |
| 2004/0082956 A1 | 4/2004 | Baldwin et al. |
| 2004/0088004 A1 | 5/2004 | Rosch |
| 2004/0098051 A1 | 5/2004 | Fallin et al. |
| 2004/0098053 A1 | 5/2004 | Tran |
| 2004/0116843 A1 | 6/2004 | Chan |
| 2004/0172062 A1 | 9/2004 | Burkhart |
| 2004/0267317 A1 | 12/2004 | Higgins et al. |
| 2005/0033362 A1 | 2/2005 | Grafton |
| 2005/0033364 A1 | 2/2005 | Gregoire et al. |
| 2005/0149122 A1 | 7/2005 | McDevitt et al. |
| 2005/0245932 A1 | 11/2005 | Fanton et al. |
| 2005/0277986 A1 | 12/2005 | Foerster et al. |
| 2006/0074438 A1 | 4/2006 | Chan |
| 2006/0079904 A1 | 4/2006 | Thal |
| 2006/0142784 A1 | 6/2006 | Kontos |
| 2006/0149258 A1 | 7/2006 | Sousa |
| 2006/0155328 A1 | 7/2006 | Foerster |
| 2006/0241619 A1 | 10/2006 | Cerundolo |
| 2006/0241658 A1 | 10/2006 | Cerundolo |
| 2006/0247641 A1 | 11/2006 | Re et al. |
| 2006/0271060 A1 | 11/2006 | Gordon |
| 2006/0282081 A1 | 12/2006 | Fanton et al. |
| 2006/0282082 A1 | 12/2006 | Fanton et al. |
| 2006/0282083 A1 | 12/2006 | Fanton et al. |
| 2006/0293691 A1 | 12/2006 | Mitra et al. |
| 2006/0293710 A1 | 12/2006 | Foerster et al. |
| 2007/0005067 A1* | 1/2007 | Dross ............... A61B 17/17 606/232 |
| 2007/0005068 A1 | 1/2007 | Sklar |

(56) References Cited

U.S. PATENT DOCUMENTS

| | | |
|---|---|---|
| 2007/0016251 A1 | 1/2007 | Roby |
| 2007/0021751 A1 | 1/2007 | Reay-Young et al. |
| 2007/0027475 A1 | 2/2007 | Pagedas |
| 2007/0043377 A1 | 2/2007 | Fernandez |
| 2007/0088362 A1 | 4/2007 | Bonutti et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0167950 A1 | 7/2007 | Tauro et al. |
| 2007/0173845 A1 | 7/2007 | Kim |
| 2007/0203498 A1 | 8/2007 | Gerber et al. |
| 2007/0213730 A1 | 9/2007 | Martinek et al. |
| 2007/0213770 A1 | 9/2007 | Dreyfuss |
| 2007/0219557 A1 | 9/2007 | Bourque et al. |
| 2007/0219558 A1 | 9/2007 | Deutsch |
| 2007/0288023 A1 | 12/2007 | Pellegrino et al. |
| 2008/0009904 A1 | 1/2008 | Bourque et al. |
| 2008/0033486 A1 | 2/2008 | Whittaker et al. |
| 2008/0057838 A1 | 3/2008 | Huang et al. |
| 2008/0077161 A1 | 3/2008 | Kaplan |
| 2008/0103528 A1 | 5/2008 | Zirps et al. |
| 2008/0125815 A1 | 5/2008 | Heaven et al. |
| 2008/0147063 A1 | 6/2008 | Cauldwell et al. |
| 2008/0188936 A1 | 8/2008 | Ball et al. |
| 2008/0208253 A1 | 8/2008 | Dreyfuss et al. |
| 2008/0234730 A1 | 9/2008 | Cotton et al. |
| 2008/0243174 A1 | 10/2008 | Oren et al. |
| 2008/0243177 A1 | 10/2008 | Oren et al. |
| 2008/0243178 A1 | 10/2008 | Oren et al. |
| 2008/0275453 A1 | 11/2008 | Lafosse et al. |
| 2008/0287992 A1 | 11/2008 | Tornier et al. |
| 2008/0300629 A1 | 12/2008 | Surti |
| 2009/0018561 A1 | 1/2009 | Schwartz et al. |
| 2009/0018581 A1 | 1/2009 | Anderson et al. |
| 2009/0036905 A1 | 2/2009 | Schmieding |
| 2009/0048623 A1 | 2/2009 | Lafosse et al. |
| 2009/0062819 A1 | 3/2009 | Burkhart et al. |
| 2009/0076544 A1 | 3/2009 | DiMatteo et al. |
| 2009/0099598 A1 | 4/2009 | McDevitt et al. |
| 2009/0138002 A1 | 5/2009 | Fenton |
| 2009/0149884 A1 | 6/2009 | Snyder et al. |
| 2009/0171360 A1 | 7/2009 | Whelan |
| 2009/0187216 A1 | 7/2009 | Schmieding et al. |
| 2009/0192546 A1 | 7/2009 | Schmieding et al. |
| 2009/0222039 A1 | 9/2009 | Dreyfuss et al. |
| 2009/0287246 A1 | 11/2009 | Cauldwell et al. |
| 2009/0292313 A1 | 11/2009 | Anspach et al. |
| 2009/0312782 A1 | 12/2009 | Park |
| 2009/0312794 A1 | 12/2009 | Nason et al. |
| 2009/0318960 A1 | 12/2009 | Burkhart |
| 2010/0004683 A1 | 1/2010 | Hoof et al. |
| 2010/0087872 A1 | 4/2010 | Morihara et al. |
| 2010/0100129 A1 | 4/2010 | West et al. |
| 2010/0106194 A1* | 4/2010 | Bonutti ............. A61B 17/842 606/279 |
| 2010/0121337 A1 | 5/2010 | Pandya |
| 2010/0121348 A1 | 5/2010 | Van et al. |
| 2010/0121354 A1 | 5/2010 | Pandya |
| 2010/0121375 A1 | 5/2010 | Pandya |
| 2010/0121447 A1 | 5/2010 | Troger et al. |
| 2010/0137889 A1 | 6/2010 | Oren et al. |
| 2010/0179573 A1 | 7/2010 | Levinsohn et al. |
| 2010/0198235 A1 | 8/2010 | Pierce et al. |
| 2010/0249835 A1 | 9/2010 | Schwartz et al. |
| 2010/0262184 A1 | 10/2010 | Dreyfuss |
| 2010/0292732 A1 | 11/2010 | Hirotsuka et al. |
| 2010/0318125 A1 | 12/2010 | Gerber et al. |
| 2010/0318139 A1 | 12/2010 | Beauchamp |
| 2010/0324575 A1 | 12/2010 | Chan |
| 2011/0009867 A1* | 1/2011 | Oren ................. A61B 17/0485 606/232 |
| 2011/0009884 A1 | 1/2011 | Kaplan |
| 2011/0022087 A1 | 1/2011 | Cerundolo |
| 2011/0028997 A1 | 2/2011 | Gregoire et al. |
| 2011/0071550 A1 | 3/2011 | Diduch et al. |
| 2011/0106013 A1 | 5/2011 | Whittaker et al. |
| 2011/0106124 A1 | 5/2011 | Beauchamp |
| 2011/0112550 A1 | 5/2011 | Heaven et al. |
| 2011/0112576 A1 | 5/2011 | Nguyen et al. |
| 2011/0118757 A1 | 5/2011 | Pierce |
| 2011/0118762 A1 | 5/2011 | Dooney et al. |
| 2011/0152928 A1 | 6/2011 | Colleran et al. |
| 2011/0190815 A1 | 8/2011 | Saliman |
| 2011/0208198 A1 | 8/2011 | Anderson et al. |
| 2011/0224726 A1 | 9/2011 | Lombardo et al. |
| 2011/0238111 A1 | 9/2011 | Frank |
| 2011/0238112 A1 | 9/2011 | Kim et al. |
| 2011/0238113 A1 | 9/2011 | Fanton et al. |
| 2011/0245869 A1 | 10/2011 | Burkhart |
| 2011/0295279 A1* | 12/2011 | Stone ................. A61B 17/0469 606/145 |
| 2011/0301622 A1 | 12/2011 | Oren et al. |
| 2012/0041484 A1 | 2/2012 | Briganti et al. |
| 2012/0059415 A1 | 3/2012 | Sklar |
| 2012/0116451 A1 | 5/2012 | Tepic |
| 2012/0143224 A1 | 6/2012 | Chan |
| 2012/0150225 A1 | 6/2012 | Burkhart et al. |
| 2012/0150235 A1 | 6/2012 | Snyder et al. |
| 2012/0158051 A1 | 6/2012 | Foerster |
| 2012/0165868 A1 | 6/2012 | Burkhart et al. |
| 2012/0179200 A1 | 7/2012 | Cauldwell et al. |
| 2012/0197296 A1 | 8/2012 | Mayer et al. |
| 2012/0209279 A1 | 8/2012 | Snyder et al. |
| 2012/0209325 A1 | 8/2012 | Gagliano et al. |
| 2012/0245634 A1 | 9/2012 | Kaplan |
| 2012/0265219 A1 | 10/2012 | Rushdy et al. |
| 2012/0272816 A1 | 11/2012 | Ueda et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035720 A1 | 2/2013 | Perriello et al. |
| 2013/0053959 A1 | 2/2013 | Lizardi et al. |
| 2013/0060280 A1 | 3/2013 | Wolf et al. |
| 2013/0096611 A1 | 4/2013 | Sullivan |
| 2013/0103083 A1 | 4/2013 | Baird |
| 2013/0123809 A1 | 5/2013 | Murphy et al. |
| 2013/0123840 A1 | 5/2013 | Murphy et al. |
| 2013/0123842 A1 | 5/2013 | Chan et al. |
| 2013/0123843 A1 | 5/2013 | Chan et al. |
| 2013/0144335 A1 | 6/2013 | Sandow |
| 2013/0150885 A1 | 6/2013 | Dreyfuss |
| 2013/0165972 A1 | 6/2013 | Sullivan |
| 2013/0178854 A1 | 7/2013 | Sholev et al. |
| 2013/0190782 A1 | 7/2013 | Nason |
| 2013/0190871 A1 | 7/2013 | Markarian |
| 2013/0197575 A1 | 8/2013 | Karapetian et al. |
| 2013/0197577 A1 | 8/2013 | Wolf et al. |
| 2013/0197578 A1 | 8/2013 | Gregoire et al. |
| 2013/0204253 A1 | 8/2013 | Oren et al. |
| 2013/0204298 A1 | 8/2013 | Graul et al. |
| 2013/0204299 A1 | 8/2013 | Mantovani et al. |
| 2013/0211429 A1 | 8/2013 | Snyder et al. |
| 2013/0218273 A1 | 8/2013 | Bull et al. |
| 2013/0226231 A1 | 8/2013 | Weinert et al. |
| 2013/0267998 A1 | 10/2013 | Vijay et al. |
| 2013/0296936 A1 | 11/2013 | Burkhart |
| 2013/0325011 A1 | 12/2013 | Cleveland et al. |
| 2013/0338710 A1 | 12/2013 | Heaven et al. |
| 2013/0345711 A1 | 12/2013 | Mehta et al. |
| 2013/0345749 A1 | 12/2013 | Sullivan et al. |
| 2013/0345750 A1 | 12/2013 | Sullivan |
| 2014/0046369 A1 | 2/2014 | Heaven et al. |
| 2014/0046443 A1 | 2/2014 | McKernan et al. |
| 2014/0081320 A1 | 3/2014 | Sengun et al. |
| 2014/0107672 A1 | 4/2014 | Dross |
| 2014/0107700 A1 | 4/2014 | Baird et al. |
| 2014/0114317 A1 | 4/2014 | Oren et al. |
| 2014/0114411 A1 | 4/2014 | Baird et al. |
| 2014/0121467 A1 | 5/2014 | Vayser et al. |
| 2014/0134802 A1 | 5/2014 | Lin et al. |
| 2014/0135802 A1 | 5/2014 | Mantovani |
| 2014/0163612 A1 | 6/2014 | Hootstein |
| 2014/0171948 A1 | 6/2014 | Griffiths et al. |
| 2014/0172016 A1 | 6/2014 | Housman |

(56) References Cited

U.S. PATENT DOCUMENTS

| | | |
|---|---|---|
| 2014/0186416 A1 | 7/2014 | Boutros |
| 2014/0186418 A1 | 7/2014 | Boutros |
| 2014/0194906 A1 | 7/2014 | Topper et al. |
| 2014/0207189 A1 | 7/2014 | Foerster et al. |
| 2014/0214038 A1 | 7/2014 | Sholev et al. |
| 2014/0222072 A1 | 8/2014 | Gerber et al. |
| 2014/0243892 A1 | 8/2014 | Choinski |
| 2014/0257384 A1 | 9/2014 | Dreyfuss et al. |
| 2014/0276984 A1* | 9/2014 | Burbank .......... A61B 17/12013 606/144 |
| 2014/0288594 A1 | 9/2014 | Shaefers et al. |
| 2014/0303625 A1 | 10/2014 | Sholev et al. |
| 2014/0324100 A1 | 10/2014 | Burkhart |
| 2014/0343605 A1 | 11/2014 | Lunn et al. |
| 2014/0364876 A1 | 12/2014 | White et al. |
| 2014/0364905 A1 | 12/2014 | Lunn et al. |
| 2014/0364907 A1 | 12/2014 | White et al. |
| 2014/0379027 A1 | 12/2014 | Dreyfuss et al. |
| 2014/0379028 A1 | 12/2014 | Lo |
| 2015/0005773 A1 | 1/2015 | Oren et al. |
| 2015/0005817 A1 | 1/2015 | Snyder et al. |
| 2015/0005818 A1 | 1/2015 | McDevitt et al. |
| 2015/0025552 A1 | 1/2015 | Stoll |
| 2015/0032155 A1 | 1/2015 | Dreyfuss et al. |
| 2015/0032157 A1 | 1/2015 | Dooney et al. |
| 2015/0045795 A1 | 2/2015 | Sholev et al. |
| 2015/0051645 A1 | 2/2015 | Green et al. |
| 2015/0066079 A1 | 3/2015 | Schmieding |
| 2015/0066080 A1 | 3/2015 | Olson et al. |
| 2015/0066081 A1 | 3/2015 | Martin |
| 2015/0088196 A1 | 3/2015 | Kaplan |
| 2015/0119937 A1 | 4/2015 | Lunn et al. |
| 2015/0141998 A1 | 5/2015 | Kiapour et al. |
| 2015/0150551 A1 | 6/2015 | Paulk et al. |
| 2015/0157312 A1 | 6/2015 | Burkhart et al. |
| 2015/0196388 A1 | 7/2015 | Housman et al. |
| 2015/0216522 A1 | 8/2015 | Ticker |
| 2015/0216542 A1 | 8/2015 | Libby et al. |
| 2015/0223926 A1 | 8/2015 | Foerster et al. |
| 2015/0245831 A1 | 9/2015 | Sullivan |
| 2015/0297211 A1 | 10/2015 | Sullivan et al. |
| 2015/0297274 A1 | 10/2015 | Dreyfuss et al. |
| 2015/0313586 A1 | 11/2015 | Burkhart et al. |
| 2015/0327849 A1 | 11/2015 | Dooney et al. |
| 2015/0335327 A1 | 11/2015 | Ferguson et al. |
| 2015/0351752 A1 | 12/2015 | Rousseau et al. |
| 2015/0359533 A1 | 12/2015 | Kaplan |
| 2016/0015380 A1 | 1/2016 | Sholev et al. |
| 2016/0296224 A1 | 10/2016 | Snell et al. |
| 2016/0338689 A1 | 11/2016 | Baird |
| 2016/0338693 A1 | 11/2016 | Graul et al. |
| 2017/0014172 A1 | 1/2017 | Fallin et al. |
| 2017/0100182 A1 | 4/2017 | Shah et al. |
| 2018/0078251 A1 | 3/2018 | Copple et al. |
| 2021/0177394 A1 | 6/2021 | Rippe et al. |

FOREIGN PATENT DOCUMENTS

| | | |
|---|---|---|
| WO | 03/65904 A1 | 8/2003 |
| WO | 2004/049958 A1 | 6/2004 |
| WO | 2009/018565 A1 | 2/2009 |
| WO | 2009/042951 A1 | 4/2009 |
| WO | 2009/055800 A1 | 4/2009 |
| WO | 2009/076526 A1 | 6/2009 |
| WO | 2010/005749 A1 | 1/2010 |
| WO | 2010/009217 A1 | 1/2010 |
| WO | 2010/056786 A2 | 5/2010 |
| WO | 2010/056787 A2 | 5/2010 |
| WO | 2011/056701 A1 | 5/2011 |
| WO | 2011/059995 A2 | 5/2011 |
| WO | 2011/060022 A2 | 5/2011 |
| WO | 2011/060437 A1 | 5/2011 |
| WO | 2011/133233 A1 | 10/2011 |
| WO | 2012/024446 A2 | 2/2012 |
| WO | 2012/052891 A1 | 4/2012 |
| WO | 2012/129388 A1 | 9/2012 |
| WO | 2013/014553 A1 | 1/2013 |
| WO | 2013/027210 A1 | 2/2013 |
| WO | 2013/052128 A1 | 4/2013 |
| WO | 2013/112449 A1 | 8/2013 |
| WO | 2013/151817 A1 | 10/2013 |
| WO | 2013/181212 A1 | 12/2013 |
| WO | 2014/018946 A1 | 1/2014 |
| WO | 2014/051930 A2 | 4/2014 |
| WO | 2014/055678 A1 | 4/2014 |
| WO | 2014/059378 A1 | 4/2014 |
| WO | 2014/066116 A1 | 5/2014 |
| WO | 2014/071052 A1 | 5/2014 |
| WO | 2014/071066 A1 | 5/2014 |
| WO | 2015/005951 A1 | 1/2015 |
| WO | 2015/008176 A2 | 1/2015 |
| WO | 2015/017426 A1 | 2/2015 |
| WO | 2015/031559 A1 | 3/2015 |
| WO | 2016/148941 A1 | 9/2016 |

OTHER PUBLICATIONS

Achilles SpeedBridge Surgical Technique, Arthrex, Inc., www.arthrex.com, 2013, 6 pp.

Achilles SutureBridge Surgical Technique, Arthrex, Inc., www.arthrex.com, 2014, 6 pp.

ALLThread Knotless Suture Anchor, Double Row Rotator Cuff Repair, Biomet Orthopedics, www.biomet.com, 2012, 12 pp.

Arthrex is Reaching New Heights in Rotator Cuff Repair, Arthrex, Inc., www.arthrex.com, 2007, 8 pp.

Arthrex SpeedBridge and Tornier Arthro Tunneler Biomechanical Cadavar Testing, Arthrex, Inc., 2010, 2 pp.

Arthroscopic and Mini-Open Rotator Cuff Repair Using JuggerKnot Soft Anchor-2.9 mm with ALLthread Knotless Anchor Surgical Technique, Biomet Sports Medicine, www biomet.com, 2013, 16 pp.

Arthroscopic Shoulder Repair Using the Smith & Nephew Footpring PK Suture Anchor, Smith & Nephew, Inc., www.smith-nephew.com, 2008, 12 pp.

ArthroTunneler TunnelPro System, Transosseous Rotator Cuff Repair, Tornier, Inc., www.tornier.com, 2012, 6 pp.

Biceps Tenodesis SwiveLock System Surgical Technique, Arthrex, Inc., www.arthrex.com, 2012, 6 pp.

BioRaptor Knotless Suture Anchor, Smith & Nephew, Inc., www.smith-nephew.com, 2010, 6 pp.

Carter, Sally L., et al., "Suture Performance in Standard Arthroscopic Knots—Effects of Material and Design" Smith & Nephew, Inc., www.smith-nephew.com, 2004, 4 pp.

Chu, T., et al., "Biomechanical Evaluation of Knotless Fixation Systems for Rotator Cuff Repairs", 56.sup.th Annual Meeting of the Orthopaedic Research Society, Post No. 1791, 1 pp.

Cinch Lock SS (Sports Sheath) Knotless Labrum Restoration, Stryker Corporation, www.stryker.com, 6 pp, accessed online on Jun. 22, 2022.

Comprehensive Product Offerings for your Rotator Cuff Repair, Smith & Nephew, Inc., www smith-nephew.com, 2015, 12 pp.

DeFranco, Michael J., et al., "Arthroscopic Rotator Cuff Repair Failure Resulting from Decorticiation of the Rotator Cuff Footprint: A Case Report", The American Journal of Orthopedics, Dec. 2009, pp. 32-33.

Double Row Rotator Cuff Repair using the Bio-Corkscrew Ft Surgical Technique, Arthrex, Inc., www.arthrex.com, 2007, 6 pp.

Dr. S. D. Gerber Double Row Method Surgical Technique, Stryker Corporation, www.stryker.com, 2010, 12 pp.

Efird, Chad, et al., "Knotless Single-Row Rotator Cuff Repair: A Comparative Biomechanical Study of 2 Knotless Suture Anchors", Healio.com/Orthopedics, Aug. 2013, 5 pp.

Flores, Steve, "Comparison of the Pull-Back Effect of Rotator Cuff Anchors", Arthrex, Inc., 2007, 2 pp.

Halbrecht, Jeffrey, "Versalok A New Technique for Arthroscopic Knotless Rotator Cuff Repair", 44 pp, accessed online on Jun. 22, 2022.

(56) References Cited

OTHER PUBLICATIONS

Introducing the Healix Advance Family of Suture Anchors, DePuy Mitek, Inc, 2012, 4 pp.
Knotless SutureTak Instability Repair Surgical Technique, Arthrex, Inc., www.arthex.com, 2017, 6 pp.
Mall, Nathan A., et al., "Transosseous-Equivalent Rotator Cuff Repair: A Systematic Review on the Biomechanical Importance of Tying the Medial Row", Arthroscopy: The Journal of Arthroscopic and Related Surgery, vol. 29, No. 2, Feb. 2013, pp. 377-386.
Massive Rotator Cuff Repair and Augmentation using the SpeedBridge and ArthroFlex Dermal Matrix Surgical Technique, Arthrex, Inc., www arthrex.com, 2012, 4 pp.
Multifix's Peek 5.5mm and 6.5mm Knotless Implants Technique Guide, ArthroCare Corporation, www.smith-nephew.com, 2015, 8 pp.
Nho, Shane J., et al,. "Bioabsorbable Anchors in Glenohumeral Shoulder Surgery", Arthrscopy: The Journal of Arthroscopic and Related Surgery, vol. 25, No. 7, Jul. 2009, pp. 788-793.
Opus AutoCuff Magnum X Knotless Fixation Implant with Independent Tensioning, ArthroCare Sports Medicine, www.arthrocaresportsmedicine.com, 2009, 2 pp.
Pull-Out Strength Comparison of Arthrex to Mitek Suture Anchors, Arthrex Research and Development, Arthrex, Inc., 2010, 1 pp.
Quattro Shoulder System—Innovative Rotator Cuff Solutions, https://www.zimmerbiomet.com/en/products-and-solutions/specialties/sports-medicine/quattro-x-suture-anchors.html#04-Info, 12 pp, accessed online Jun. 22, 2022.
Quickdraw Knotless Suture Anchor System Surgical Technique, Writght Medical Technology, Inc. www.wmt.com, 2011, 28 pp.
ReelX STT Knotless Anchor System, Stryker Corporation, www.stryker.com, 2010, 4 pp.
Revolutionizing Orthopedic Surgery, FiberWire Braided Composite Suture, Arthrex, Inc., www.arthrex.com, 2012, 8 pp.
Shoulder Restoration System, PopLok Knotless Suture Anchor, ConMed Linvatec, www.linvatec.com, 8 pp, 2013.
SpeedBridge and SpeedFix Knotless Rotator Cuff Repair using the SwiveLock C and FiberTape Surgical Technique, Arthrex, Inc., www.arthrex.com, 2013, 8 pp.
Supplementary European Search Report dated Jun. 26, 2019 for corresponding European Application No. EP16833705.
Surgical Technique Sharc-FT and Taylor Stitcher Transosseus Devices for Fast Rotator Cuff Repair, NCS Lab Medical Devices Factory, 14 pp., accessed online Jun. 22, 2022, https://ncs-company.com/en/medical-devices/sport-medicine/.
SutureBridge Double Row Rotator Cuff Repair Surgical Technique, Arthrex, Inc., www.arthrex.com, 2013, 6 pp.
SwiveLock and FiberChain Knotless Rotator Cuff Repair Surgical Technique, Arthrex, Inc, www.arthrex.com, 2011, 8 pp.
The DoublePlay Biocomposite Suture Anchor, ArthroCare Sports Medicine, www.arthrocaresportsmedicine.com, 2009, 12 pp.
The Fully Threaded Family of Soft Tissue Repair Anchors, Arthrex, Inc., www.arthrex.com, 2012, 6 pp.
The Next Generation in Shoulder & Elbow Repair and Reconstruction Technology, Arthrex, Inc., www.arthrex.com, 2014, 56 pp.
The Opus AutoCuff System for Rotatpr Cuff Repair, ArthroCare Sports Medicine, www.arthrocaresportsmedicine.com, 2006, 8 pp.
The Opus TwinLock Knotless Fixation System, ArthroCare Sports Medicine, www.arthrocaresportsmedicine.com, 2010, 2 pp.
Versalok Peek, the New, 100% Radiolucent, Self-Punching, Knotless Anchor, DePuy Mitek, Inc., 2010, 4 pp.
Versalok, The Next Generation in Rotator Cuff Repair, DePuy Mitek, 18 pp., 2007.
U.S. Appl. No. 15/887,095, filed Feb. 2, 2018.
U.S. Appl. No. 15/211,764, filed Jul. 15, 2016.
U.S. Appl. No. 15/211,673, filed Jul. 15, 2016.

\* cited by examiner

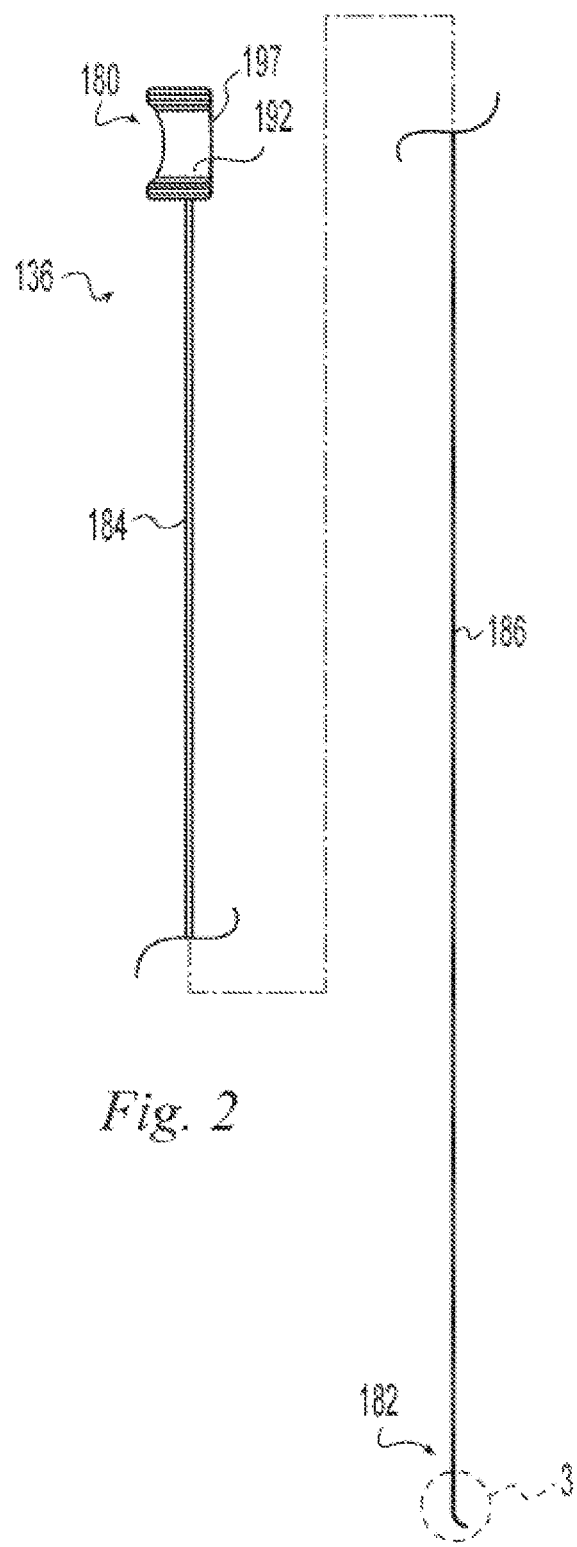
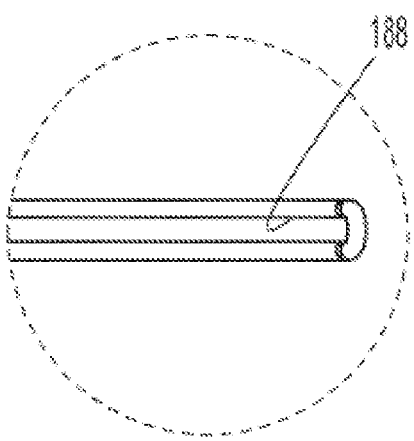
Fig. 2
Fig. 3
Fig. 4

TRANSOSSEOUS GUIDE AND METHOD

CROSS-REFERENCE TO RELATED APPLICATIONS

This application is a divisional application of U.S. patent application Ser. No. 15/887,095, filed Feb. 2, 2018 entitled TRANSOSSEOUS GUIDE AND METHOD, which is a continuation-in-part of U.S. patent application Ser. No. 15/211,764, filed Jul. 15, 2016 entitled TRANSOSSEOUS GUIDE, which issued on Apr. 16, 2019 as U.S. Pat. No. 10,258,401, which claims the benefit of U.S. Provisional Application No. 62/193,888, filed Jul. 17, 2015 entitled TRANSOSSEOUS GUIDE AND METHOD. U.S. patent application Ser. No. 15/887,095, filed Feb. 2, 2018 entitled TRANSOSSEOUS GUIDE AND METHOD is also a continuation-in-part of U.S. patent application Ser. No. 15/211,673, filed Jul. 15, 2016 entitled TRANSOSSEOUS METHOD, which issued on Dec. 18, 2018 as U.S. Pat. No. 10,154,868, which also claims the benefit of U.S. Provisional Application No. 62/193,888 filed Jul. 17, 2015 entitled TRANSOSSEOUS GUIDE AND METHOD. Each of the above named applications is incorporated by reference, as if set forth herein in its entirety.

TECHNICAL FIELD

The present disclosure relates to transosseous guides and methods for transosseous attachments.

BACKGROUND

A variety of surgical procedures require the attachment of something relative to a surgical site. For example, in surgery relating to the skeletal system, it is often advantageous to attach soft tissue, suture, implants, and/or other items in or adjacent to a joint. For example, soft tissues such as ligaments, tendons, fascia, other capsular material, and/or muscle may be attached to an adjacent bone. Such soft tissues may be adjacent to bones at skeletal joints including but not limited to the joints of the hands and feet, ankle, wrist, knee, elbow, hip, shoulder, and spine. For example, it is often advantageous to pass a suture through a portion of a bone to form a transosseous attachment to the bone.

SUMMARY

Examples of the present disclosure provide instruments and methods for surgical transosseous attachment to a bone.

In one example of the present disclosure, a system for placing a flexible member transosseously through first and second transverse, intersecting bone tunnels may include a guide body having a guide body handle portion and a longitudinal guide body passage. The system may also include a first tunnel member engaged with the guide body that includes a proximal end, a distal end, a first longitudinal passage extending through the first tunnel member, at least one curved portion nearer the distal end of the first tunnel member than the proximal end of the first tunnel member, and a first guide axis associated with the distal end of the first tunnel member, where at least a portion of the first longitudinal passage near the distal end of the first tunnel member is coaxial with the first guide axis. The system may also include a second tunnel member engaged with the longitudinal guide body passage that includes a proximal end, a distal end, and a second longitudinal passage extending at least partway through the second tunnel member. The second longitudinal passage may be coaxial with a second guide axis defined by the longitudinal guide body passage when the second tunnel member is engaged with the longitudinal guide body passage and at least a portion of the first longitudinal passage near the proximal end of the first tunnel member may be parallel to the second guide axis. The system may also include a passer operable to extend from the proximal end of the first tunnel member, through the distal end of the first tunnel member, through the distal end of the second tunnel member, and to the proximal end of the second tunnel member in one continuous path.

In another example of the present disclosure, a system for placing a member transosseously through first and second bone tunnels may include a guide body with a longitudinal guide body passage. The system may also include a first tunnel member engaged with the guide body that has a proximal end, a distal end, and a first longitudinal passage extending through the first tunnel member. The system may also include a second tunnel member engaged with the longitudinal guide body passage that has a proximal end, a distal end, and a second longitudinal passage extending at least partway through the second tunnel member. The system may also include a passer operable to extend from the proximal end of the first tunnel member, through the distal end of the first tunnel member, through the distal end of the second tunnel member, and to the proximal end of the second tunnel member in one continuous path.

In another example of the present disclosure, a method for placing a member transosseously through first and second transverse, intersecting bone tunnels that includes inserting a first tunnel member into a bone along a first insertion axis, the first tunnel member having a proximal end, a distal end, and a first longitudinal passage extending through the first tunnel member. The method may also include inserting a second tunnel member into the bone along a second insertion axis that intersects the first insertion axis, the second tunnel including a proximal end, a distal end, and a second longitudinal passage extending at least partway through the second tunnel member. The method may also include inserting a passer through the first and second tunnel members in one continuous motion until the passer extends through the first longitudinal passage, the second longitudinal passage, out of the proximal end of the first tunnel member, and out of the proximal end of the second tunnel member.

BRIEF DESCRIPTION OF THE DRAWINGS

Various examples of the present disclosure will be discussed with reference to the appended drawings. These drawings depict only illustrative examples of the present disclosure and are not to be considered limiting of its scope.

FIG. 2 is a side elevation view of an example of a passer used with the instrument of FIG. 1;

FIG. 3 is a detail side elevation view of the tip of the passer of FIG. 2;

FIG. 4 is a detail front elevation view of the tip of the passer of FIG. 2;

DETAILED DESCRIPTION

Figure 1:
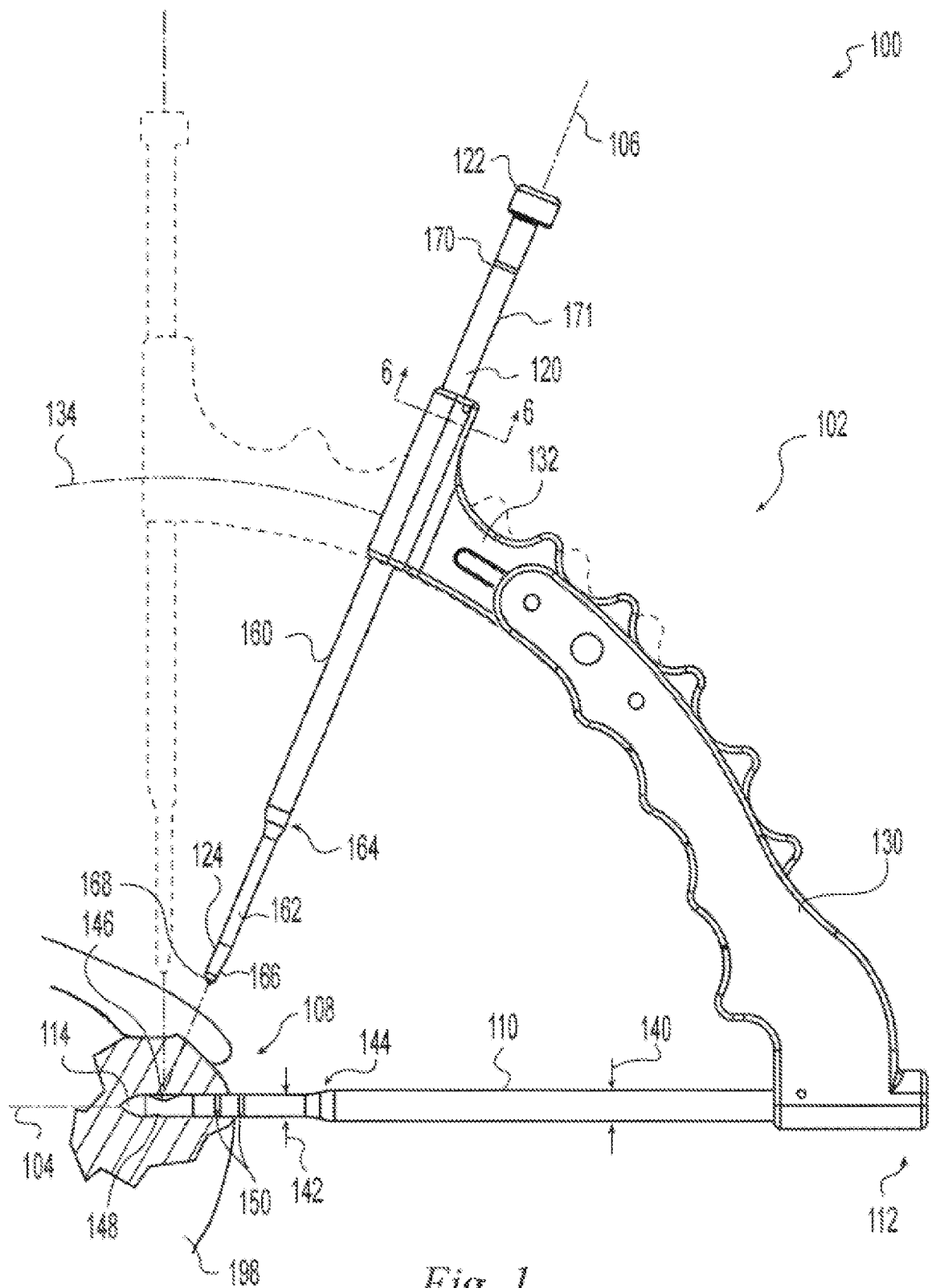
FIG. 1 is a side elevation view of an example of the present disclosure illustrating an instrument engaged with a bone, the bone being shown in partial section.

The following illustrative examples depict instruments and methods to form a tunnel through a bone and pass a member through the bone tunnel. The illustrative examples depict passing a round suture through a bone tunnel to attach soft tissue to the bone. However, the instruments and methods of the present disclosure may be used to pass other elements through a bone tunnel including, suture passers, suture tapes, cables, soft tissues, grafts, and other elements. Examples of instruments and methods of the present disclosure may be used to pass any member through any bone, at surgical sites anywhere in a patient's body, and for any purpose. The terms "suture" and "suture strand" are used herein to mean any strand or flexible member, natural or synthetic, able to be passed through a bone tunnel and useful in a surgical procedure. The term "transverse" is used herein to mean to cross at an angle; i.e. not parallel. The term includes, but is not limited to right angles.

FIGS. 1-8 depict examples of a guide and a passer for forming intersecting bone tunnels in a bone 198 and passing a flexible element through the tunnels. The exemplary guide 100 includes a guide body 102 defining a first insertion or guide axis 104 and a second insertion or guide axis 106 intersecting at a location 108 spaced from the guide body.

A first tunnel member 110 is engageable with the guide body 102 coaxial with the first guide axis 104 and includes a proximal end 112, a distal end 114, and a first longitudinal passage 116 (FIG. 7) at least partway through the first tunnel member 110.

A second tunnel member 120 is engageable with the guide body 102 coaxial with the second guide axis 106 and includes a proximal end 122, a distal end 124, and a second longitudinal passage 126 (FIG. 7) at least partway through the second tunnel member 120.

A passer 136 (FIG. 2) is operable to extend from the proximal end 122 of the second tunnel member 120, through the distal end 124 of the second tunnel member 120, through the distal end 114 of the first tunnel member 110, and to the proximal end 112 of the first tunnel member 110 in one continuous path. The passer 136 may then be used to pull a flexible member or element such as, for example, a passing suture or a repair suture through the tunnel members 110, 120 to pass the flexible element through, for example, a bone.

In the illustrative embodiment of FIGS. 1-8, the guide body 102 is made up of first and second arc members 130, 132. The first and second arc members 130, 132 are joined in sliding relationship along an arc shaped path 134 of constant radius such that the guide 100 is adjustable between a first position (shown in solid lines in FIG. 1) in which the first guide axis and the second guide axis define a first angle between them and a second position (shown in dashed lines in FIG. 1) in which the first guide axis and the second guide axis define a second, larger angle between them. Preferably, the guide is continuously adjustable over a range of included angles between the first and second guide axes 104, 106 of from 20 to 110 degrees. More preferably, the range is 60 to 90 degrees. In the illustrative example of FIGS. 1-8, the first guide axis 104 is defined by a passage in the first arc member 130 and the second guide axis 106 is defined by a passage in the second arc member 132.

The first tunnel member may include a drill guide, a punch guide, a punch, or other suitable member for forming a bone tunnel and/or for inserting into a bone tunnel. In the illustrative example of FIGS. 1-8, the first tunnel member 110 is a bone punch fixed to the guide body such as by pinning, threading, welding, or other suitable fixation method. For example, the first tunnel member 110 may be impacted into the bone 198 to form a bone tunnel in the bone. In the illustrative example of FIGS. 1-8, the first tunnel member 110 includes a cylindrical body having a first, larger diameter 140 near its proximal end 112 and a second, smaller diameter 142 near its distal end with a tapered transition region 144 between the two diameters. The cylindrical body defines a first outer side wall and a first recess or side opening 146 (FIG. 7) in the first side wall nearer the distal end 114 than the proximal end 112. The second guide axis 106 passes through the first side opening 146 for every angle in the range of adjustment of the first and second arc members 130, 132. The first longitudinal passage 116 extends from the proximal end 112 of the first tunnel member 110 toward the distal end 114 and communicates with the first side opening 146. A relief opening 148 in the side wall is positioned opposite the first side opening 146 and communicates with the first longitudinal passage 116 and the first side opening 146. The first tunnel member 110 includes indicia 150 (FIG. 1) on the outer surface readable relative to the bone surface to indicate a depth of penetration of the first tunnel member 110 into the bone. In the illustrative example of FIGS. 1-8, the indicia 150 include two separate marks to indicate the appropriate depth for two different sizes of anchor. In the illustrative example of FIGS. 1-8, the first tunnel member 110 tapers to a solid, sharp point 152 distal to the first side opening 146 and the relief opening to facilitate driving the first tunnel member 110 into bone.

The second tunnel member may include a drill guide, a punch guide, a punch, or other suitable member for forming a bone tunnel and/or inserting into a bone tunnel. In the illustrative example of FIGS. 1-8, the second tunnel member 120 is a punch engageable with the guide 100 in axial sliding relationship along the second guide axis 106. For example, the second tunnel member 120 may be impacted into the bone 198 to form a bone tunnel in the bone. In the illustrative example of FIGS. 1-8, the second tunnel member 120 includes a body having a "D"-shaped proximal portion 160 and a smaller cylindrical distal portion 162 with a tapered transition region 164 between the two portions. The body defines a second outer side wall and a second side opening 166 (FIG. 7) in the first side wall nearer the distal end 124 than the proximal end 122. In the illustrative example of FIGS. 1-8, the second longitudinal passage 126 extends from the proximal end 122 of the second tunnel member 120 toward the distal end 124 of the second tunnel member 120 and communicates with the second side opening 166. The second tunnel member 120 tapers to a solid, sharp point 168 distal to the second side opening 166 to facilitate driving the second tunnel member 120 into bone. The second tunnel member 120 includes an indicator to indicate when it is engaged with the first tunnel member 110. In one example, the second tunnel member 120 includes an index mark 170 on the outer surface readable relative to the guide 100 to indicate a depth of penetration of the second tunnel member 120 into the bone. In the illustrative example of FIGS. 1-8, the distal portion 162 of the second tunnel member 120 is engageable within the first side opening 146 of the first tunnel member with the first side opening 146 and second side opening 166 in communication with one another. The index mark 170 on the second tunnel member 120 indicates when the distal end of the second tunnel member 120 is seated in the first side opening 146. In another example, the second tunnel member 120 has an elongated marker such as for example a contrasting surface 171 that is exposed to indicate when the second tunnel member is not properly seated. The surface 171 extends proximally-distally the distance of the engagement of the second tunnel member 120 with the guide body 102. When the second tunnel member 120 is properly seated, the surface 171 is covered by the guide body 102. If the second tunnel member 120 is not fully seated, the surface 171 is visible above the guide body. If the second tunnel member is inserted too far, for example if it deflects upon insertion such that it misses the first tunnel member and is driven past the first tunnel member, the surface 171 is visible below the guide body. In one example, the surface 171 includes a colored stripe, for example a red colored stripe, such that if red is visible after inserting the second tunnel member it indicates that the second tunnel member is not properly seated. For example, in FIGS. 1 and 21 the surface 171 is visible above the guide body 102 and in FIGS. 5 and 22 the surface 171 is concealed by the guide body 100.

The relief opening 148 in the first tunnel member allows bone chips or other debris to exit the first tunnel member 110 when the second tunnel member 120 engages it. In the illustrative example of FIGS. 1-8, an angled surface 172 is formed at the distal end of the second longitudinal passage 126 facing the second side opening 166. The angled surface 172 deflects the passer 136 through the second side opening 166 and into the first longitudinal passage 116 when the passer is inserted. The "D"-shape of the proximal portion 160 of the second tunnel member 120 engages the guide 100 to prevent rotation of the second tunnel member 120 as it axially translates so that the first and second side openings 146, 166 are aligned when the first and second tunnel members 110, 120 are engaged.

The length of the first and second tunnel members 110, 120 that extends from the guide body to their intersection location may be any desired length. However, it has been found by the inventors that for rotator cuff repair surgery on a human shoulder, a length of each member in the range of 2-8 inches is useful. More preferably the length is in the range of 4-6 inches. The length for each member may be the same or different. In the example of FIGS. 1-8, the length of the first tunnel member extending from the guide body is approximately 5.5 inches and the length of the second tunnel member extending from the guide body is approximately 4.5 inches.

Figures 5, 6:
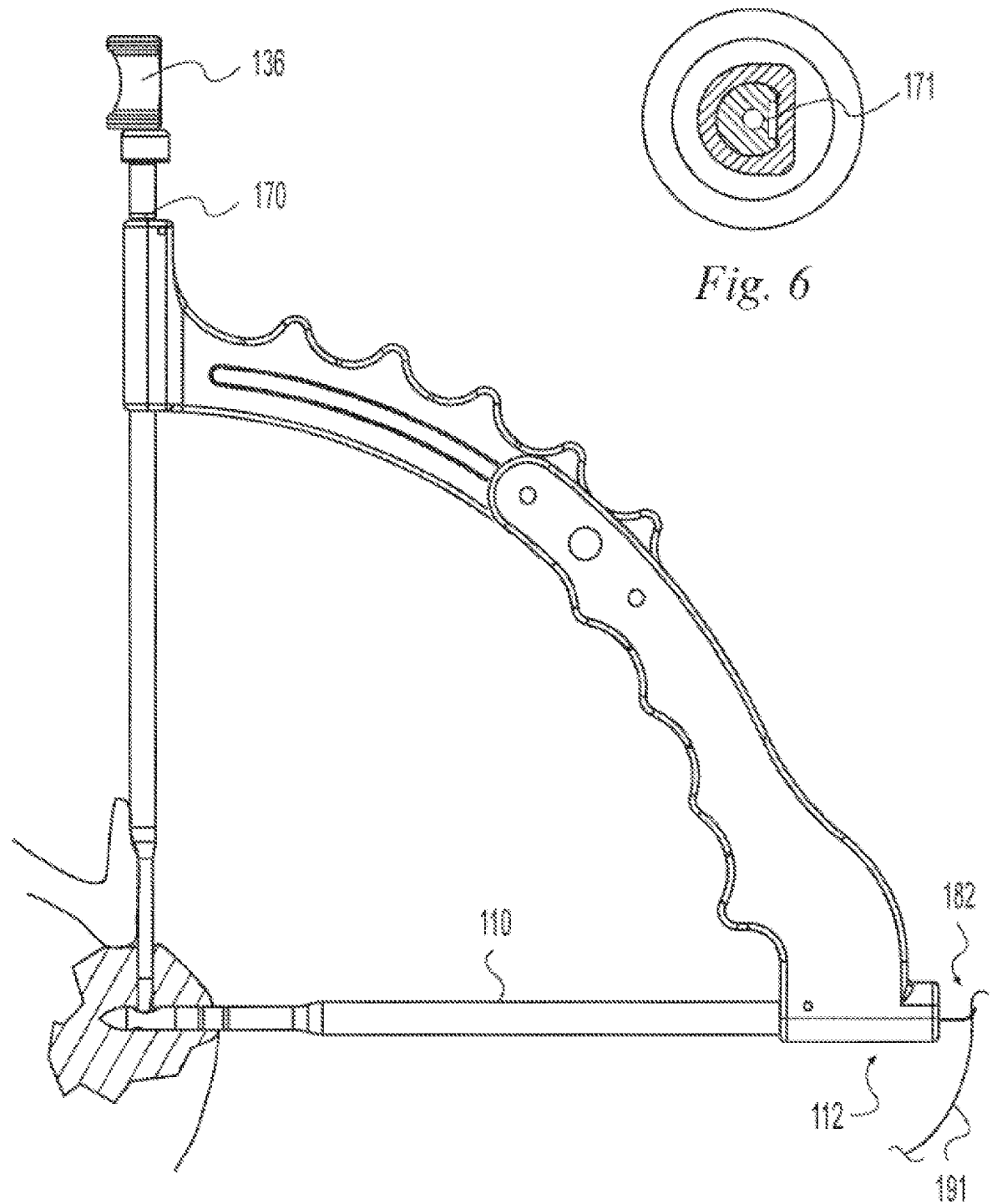
FIG. 5 is a side elevation view of the instrument of FIG. 1 engaged with a bone and the passer of FIG. 2 inserted through the instrument.
FIG. 6 is a section view taken along line 6-6 of FIG. 1.
Figure 7:
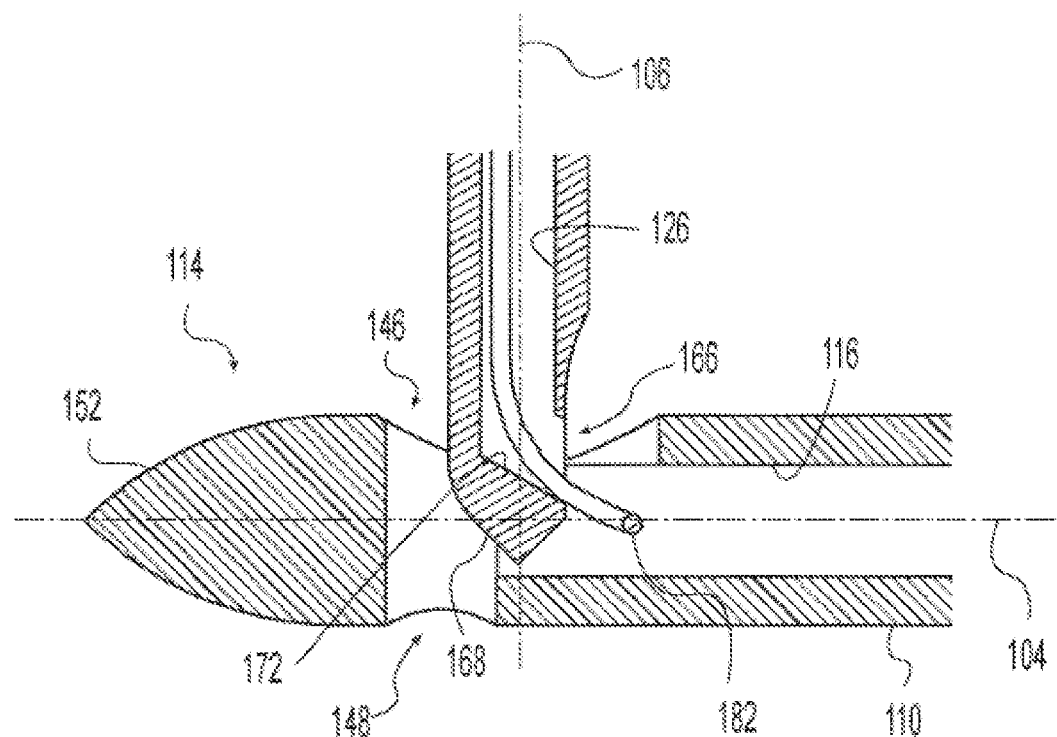
FIG. 7 is detail side section view of the instrument of FIG. 1 showing the passer engaged with the instrument in a first position.
Figure 8:
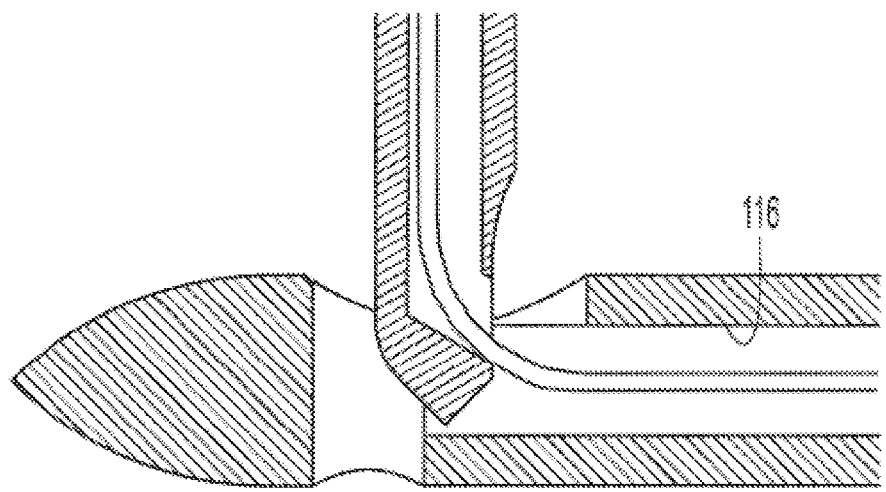
FIG. 8 is detail side section view of the instrument of FIG. 1 showing the passer engaged with the instrument in a second position.

The passer 136 includes a first, or proximal, end 180 and a second, or distal, end 182 defining a loop 188. In the illustrative example of FIGS. 1-8, the passer 136 includes a relatively rigid shaft 184 extending away from the first end and a relatively flexible wire 186 attached to the shaft 184 and extending away from the shaft 184. In one example, the shaft 184 is a tubular member and the wire 186 is crimped, bonded, soldered, welded or otherwise attached to the shaft. In the illustrative example of FIGS. 1-8, the wire 186 is formed into a loop 188 in a first plane and bent to form a curved profile 190 in a second plane perpendicular to the first plane. The curved profile 190 of the wire and the angled surface 172 at the distal end of the second longitudinal passage 126 cooperate to facilitate advancing the distal end 182 of the passer from the second longitudinal passage 126 into the first longitudinal passage 116. The passer 136 includes a handle 192 at the proximal end 180. Preferably, the passer, or at least the wire 186, is formed of a super elastic material such as nitinol, as one non-limiting example. Preferably the combined length of the shaft 184 and wire 186 is greater than the combined length of the first and second longitudinal passages 116, 126 such that the passer 136 is insertable through the first and second tunnel members 110, 120 to extend through the first and second axial passages and out of the proximal end 112 of the first tunnel member 110 and out of the proximal end 122 of the second tunnel member 120. For example, as the distal end 182 of the passer reaches the distal end of the second longitudinal passage 126, it abuts the angled surface 172 and is deflected out through the second side opening 166, through the first side opening 146 and into the first longitudinal passage 116 (FIG. 7). The curved profile 190 of the wire and angled surface 172 facilitate the transition of the wire 186 from the second tunnel member 120 to the first tunnel member 110 and promote passage even when the first and second tunnel members 110, 120 are engaged at an acute angle. The passer is further advanced to move the distal end 182 of the passer through the second longitudinal passage and out the proximal end 112 of the first tunnel member 110 (FIG. 5). A member 191, e.g. a suture, may be placed in the loop 188 at the distal end 182 of the passer and the passer 136 may be retrieved to pull the member 191 through the first longitudinal passage 116, through the first side opening 146, through the second side opening 166, through the second longitudinal passage 126 and out the proximal end of the second longitudinal passage 126. The passer handle includes an indicator, for example a flat surface 197, to indicate to a user the orientation of the bent loop 188 so that the user can orient it to engage the angled surface 172. Alternatively, or in addition, the passer may be keyed to the second tunnel member to permit only one orientation.

Figure 9:
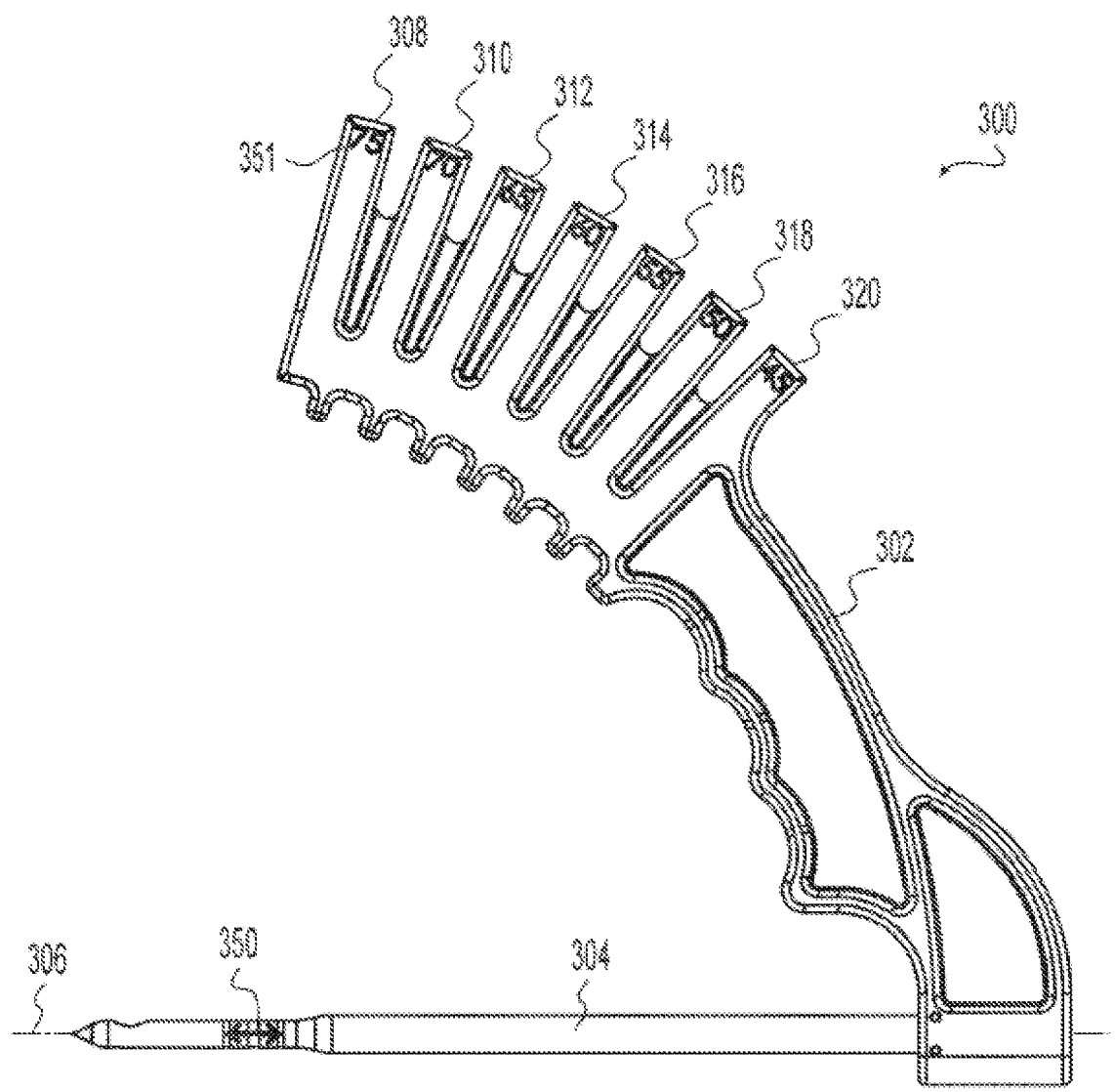
FIG. 9 is a side elevation view of an example of the present disclosure illustrating an alternative arrangement of the instrument of FIG. 1.
Figure 10:
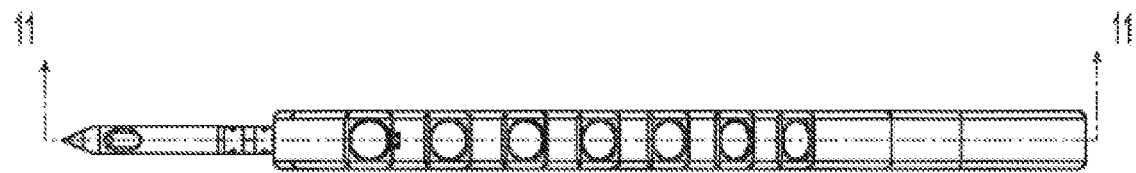
FIG. 10 is a top plan view of the instrument of FIG. 9.
Figure 11:
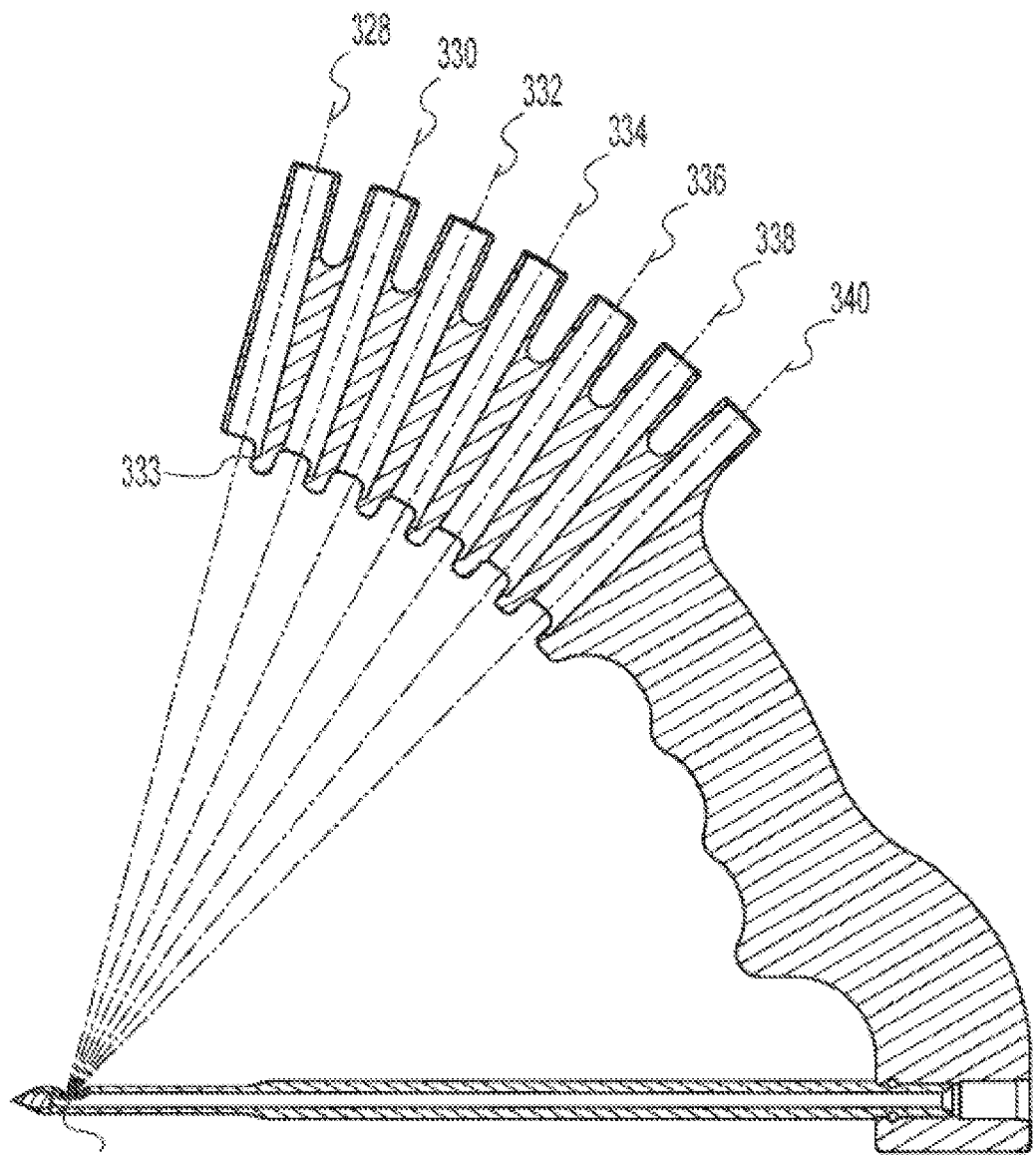
FIG. 11 is a section view taken along line 11-11 of FIG. 10.

FIGS. 9-11 illustrate another example of a guide instrument 300 similar to that of FIG. 1 but showing a different arrangement of the second guide axis. The guide body 302 includes a first tunnel member 304 like the first tunnel member in the example of FIG. 1 that defines a first guide axis 306 as with the example of FIG. 1. However, the guide body is a unitary body having a plurality of receivers 308, 310, 312, 314, 316, 318, 320 operable to receive the second tunnel member 120. Each receiver includes a passage defining a guide axis. Any number of receivers may be included at any desired spacing to provide a desired selection of guide angles relative to the first guide axis. In the example of FIGS. 9-11, seven receivers are provided defining a second guide axis 328, a third guide axis 330, a fourth guide axis 332, a fifth guide axis 334, a sixth guide axis 336, a seventh guide axis 338, and an eighth guide axis 340. Each of the second through eighth guide axes intersects the first guide axis 304 at the same location spaced from the guide body and each can selectively receive the second tunnel member. In the example of FIGS. 9-11, each of the second through eighth guide axes intersects a side opening 346 in the first tunnel member like the side opening 146 in the example of FIG. 1. A surface 333 formed at the distal end of each receiver engages the flat side of the "D"-shaped second tunnel member 120 to prevent rotation of the second tunnel member 120 within the receiver so that the first and second side openings 146, 346 are properly aligned when the first and second tunnel members are engaged.

In the example of FIGS. 9-11, the second through eighth guide axes are equally spaced and define angles of 45 degrees to 75 degrees relative to the first guide axis 306. Indicia 350 on the first tunnel member 304 indicates an insertion depth range suitable for a fastener, for example a knotless fastener. Indicia 351 on each receiver indicates the angle corresponding to each receiver. The spacing can be any desired spacing and can be uniform or non-uniform to provide a range of angles useful to the user. The inventors have found the spacing and range shown in the example to be suitable for typical rotator cuff procedures of the human shoulder.

For other applications, such as for example for attaching soft tissue to a bone adjacent a knee joint, ankle, or other location, different spacing and angular range may be desirable. Similarly, the length of the first and second tunnel member may be varied. For example, for repairing a torn Achilles tendon, a guide having an angular range of 50 to 80 degrees has been found suitable with either a sliding adjustable guide like that of FIG. 1 or a unibody guide like that of FIG. 9. In a unibody guide, four receivers defining axes at 50, 60, 70 and 80 degrees relative to the first guide axis have been found to be suitable. Any length of first and second tunnel members may be used. However, for repairing a torn Achilles tendon, shorter lengths may advantageously be used. For example, first and second tunnel members each extending from the guide body a distance in the range of two to three inches has been found suitable.

Figures 12, 13:
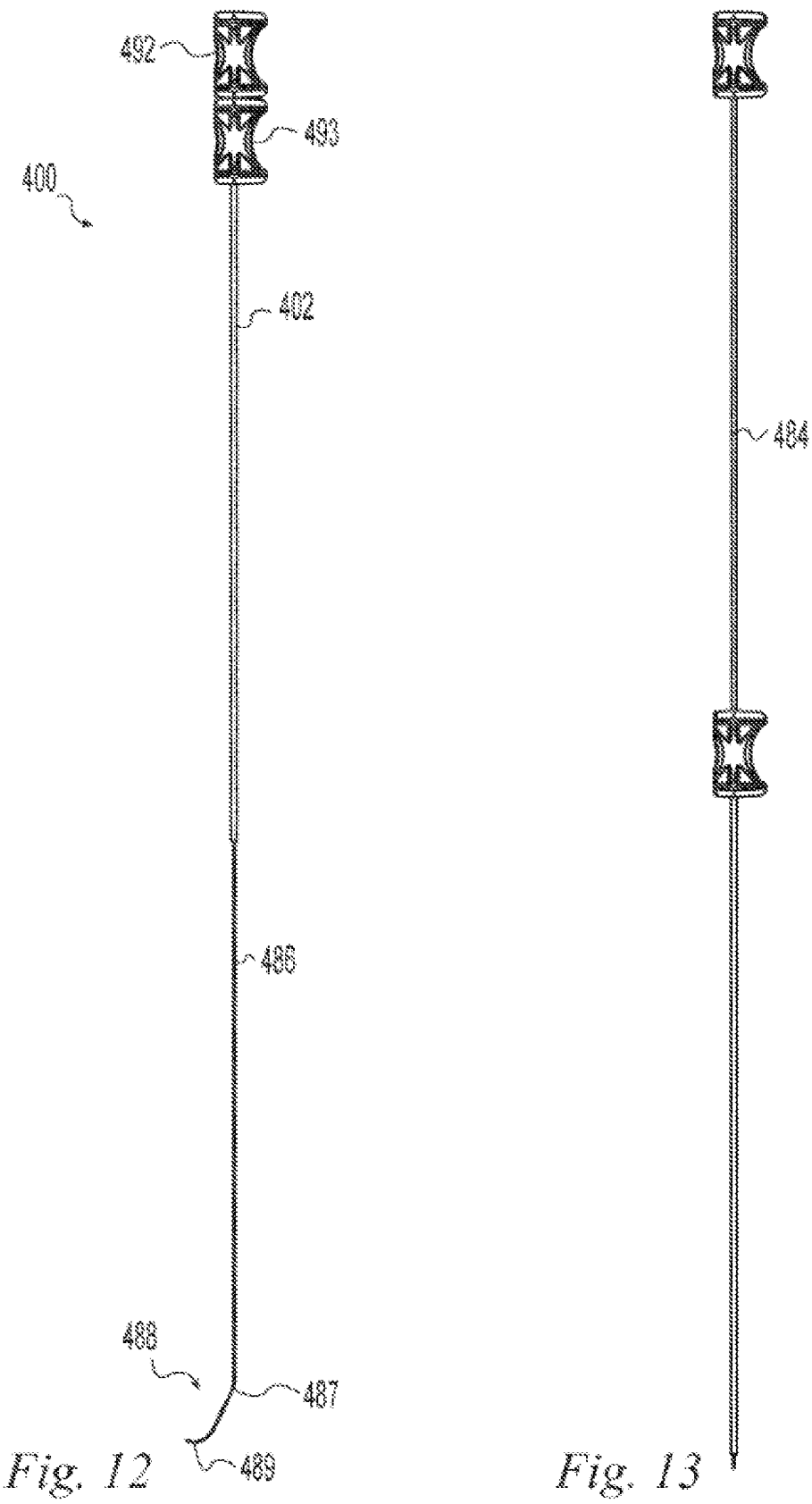
FIG. 12 is a side elevation view of an example of the present disclosure illustrating an alternative arrangement of the passer of FIG. 2 in a first position.
FIG. 13 is a side elevation view of the example of FIG. 12 in a second position.

FIGS. 12-13 illustrate another arrangement for a passer 400 similar to that of FIG. 2. The passer 400 includes an outer tube 402 engaged coaxially with the shaft 484 in axial sliding relationship and moveable relative to the shaft from a first position in which the outer tube encloses a portion of the wire length (FIG. 13) and a second position in which the outer tube encloses less of the wire length (FIG. 12). The outer tube is relatively rigid relative to the wire 486. The outer tube aids in inserting the passer 400 into the second tunnel member by holding the wire 486 in a straight and rigid configuration when the tube is in the first position. The outer tube may enclose any portion of the wire length in the first position to aid in inserting the passer. Preferably, in the first position, the outer tube encloses more than one-half of the wire length; more preferably 60 to 100 percent of the wire length; more preferably 80 to 100 percent of the wire length; more preferably the entire wire length including all of the loop 488. In the second position, enough of the wire is exposed to allow it to extend through the side openings in the first and second tunnel members and through the first tunnel member. Preferably in the second position, the outer tube encloses less than one-half of the wire length; more preferably less than 20 percent of the wire length. The tube may be inserted into the second tunnel member while in the first position and then shaft 484 advanced to extend the wire 486 out of the outer tube 402 and through the second and first tunnel members. For example, a handle 492 on the shaft may be pressed toward a handle 493 on the outer tube to advance the wire. The loop 488 in the example of FIGS. 12 and 13 includes a first bend 487 angled away from the main portion of the wire 486 and a second bend 489 at the distal end forming a small radius. The bends 487, 489 facilitate the transition of the loop through the side openings of the tunnel members.

Figure 14:
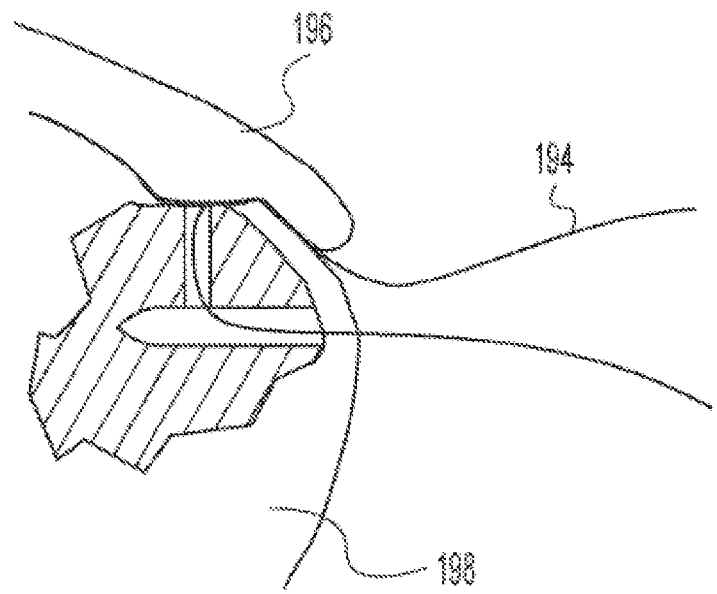
FIG. 14 is a partial sectional view of the bone of FIG. 1 after a suture has been passed and the passing instruments have been removed.
Figure 15:
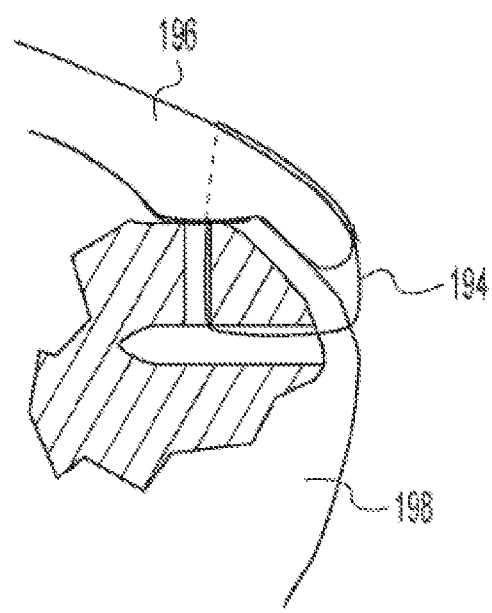
FIG. 15 is a partial sectional view illustrating the suture of FIG. 14 in use to secure a soft tissue to the bone.

The exemplary guides and methods of the present disclosure make it possible to form intersecting bone tunnels in a bone and extend, in one motion, a passer through the guide and bone tunnels from a first position external to the bone to a second position external to the bone. A first end of a member, such as a suture, may then be engaged with the passer outside of the bone tunnels. By having the engaging step outside of the bone tunnels, it may be done with simple manual manipulation of the passer loop and the first end of the member with easy access and visibility and without specialized arthroscopic instrument or procedures. The first end of the member may then be passed, in one motion, through the guide and bone tunnels from the second position external to the bone to a first position external to the bone to thread the member through the intersecting bone tunnels. The member may be used in any desirable manner. For example, a member in the form of a suture 194 may be so passed and then used to secure soft tissue 196 to the bone 198 as shown in FIGS. 14 and 15.

Figure 16:
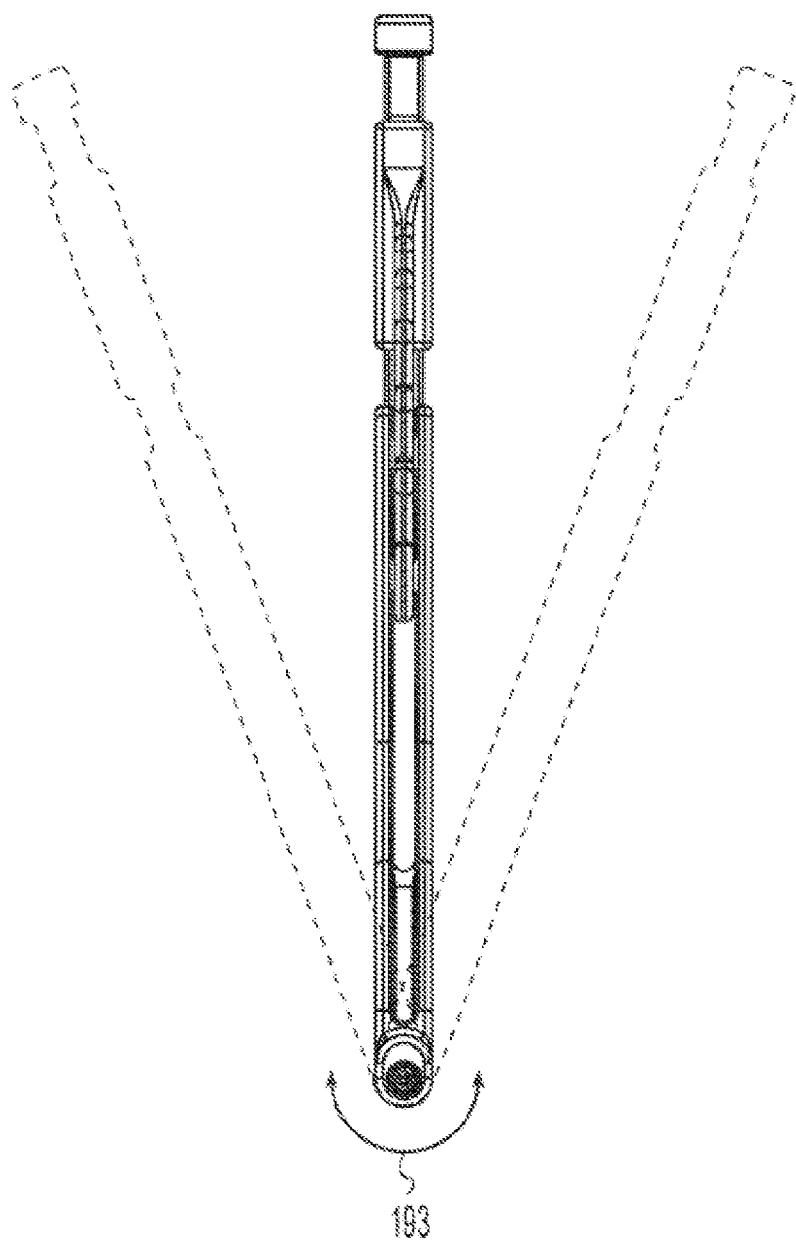
FIG. 16 is a rear elevation view of the guide of FIG. 1 illustrating how it can be rotated while engaged with a bone.
Figure 17:
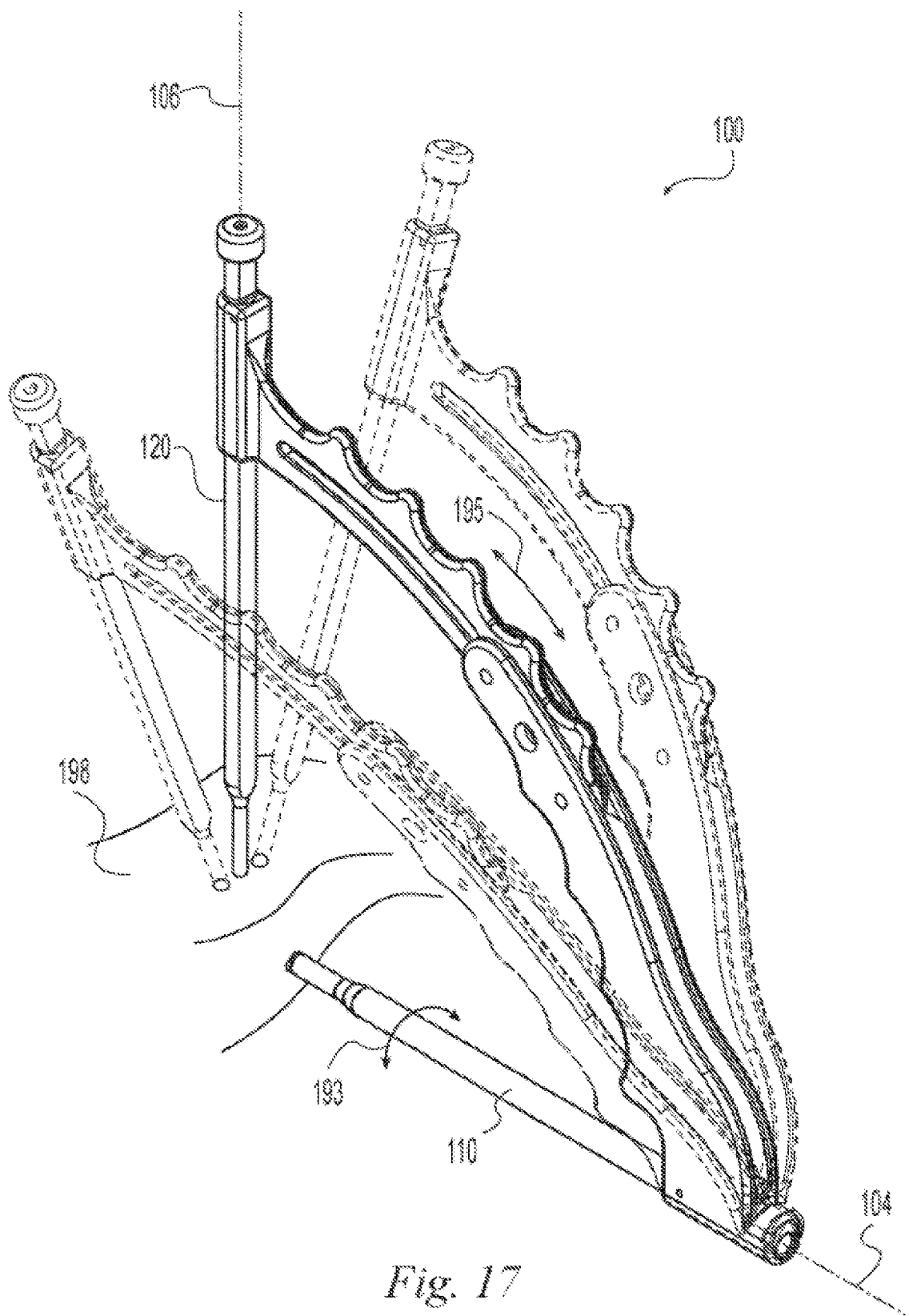
FIG. 17 is a perspective view of the guide of FIG. 1 illustrating how it can be rotated while engaged with a bone.

Referring to FIGS. 16 and 17, a guide according to examples of the present disclosure, for example guide 100 as shown in FIGS. 16 and 17, may be used to create three or more intersecting tunnels and pass flexible elements through the tunnels. For example, after passing a first flexible element through first and second intersecting tunnels in a bone 198, the second tunnel member 120 may be withdrawn from the bone. The guide 100 may be rotated about the first guide axis 104, as shown at reference numeral 193, and/or the angle between the guide axes 104 may be adjusted as shown at reference numeral 195 in FIG. 17. In a unitary guide such as the example of FIG. 9, the angle between the guide axes may be adjusted by inserting the second tunnel member in a different receiver. The second tunnel member 120 may then be inserted into the bone 198 in a new location and advanced to form a third bone tunnel intersecting the first bone tunnel. The second tunnel member 120 may be engaged with the first tunnel member 110 and the passer 136 used to pass a second flexible element through the first and third tunnels. This may be repeated as many times as desired to provide a one-to-many relationship between the first bone tunnel and the plurality of additional bone tunnels intersecting the first bone tunnel. The third and subsequent bone tunnels may be formed and the second and subsequent flexible elements may be passed while the first tunnel member 110 remains in the bone and while the first flexible element remains in the first tunnel member.

FIGS. 18-27 illustrate an example of a surgical method according to the present disclosure. In the illustrative example of FIGS. 18-27, instruments and methods of the previous examples are shown in use to place transosseous sutures to repair a rotator cuff 202 of a shoulder joint. It will be understood that any of the examples of instruments and methods of the present disclosure may be used in any combination to pass a member through a shoulder bone or other bones at a shoulder or other surgical sites and for rotator cuff repair or other surgical purposes.

Figure 18:
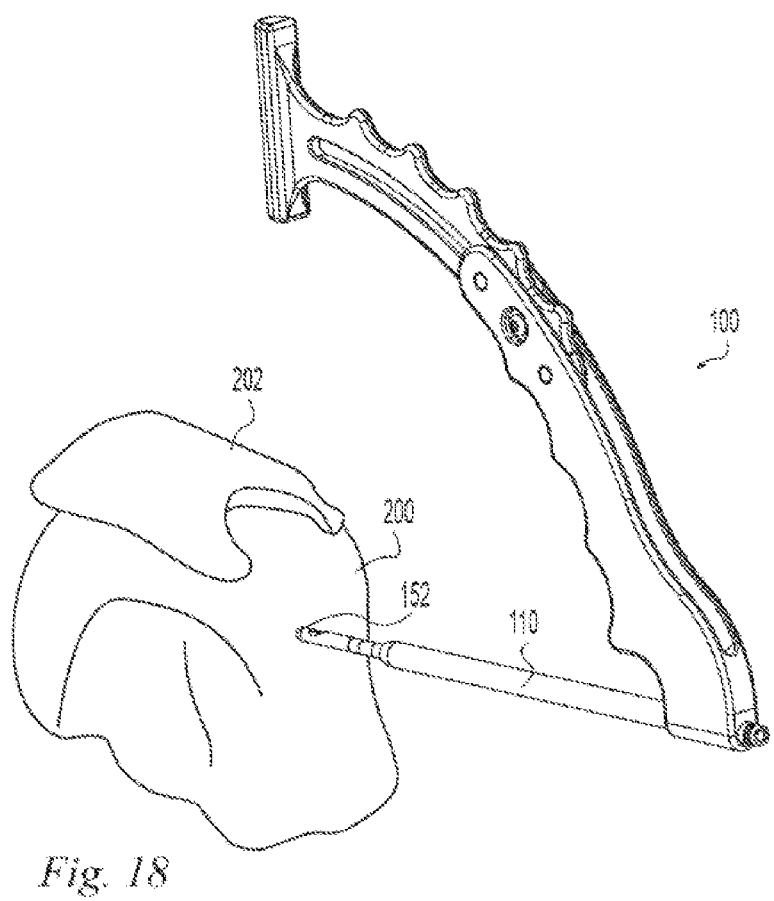
FIGS. 18-28 are perspective views of methods according to examples of the present disclosure.

Referring to FIG. 18 the guide 100 is positioned with the point 152 of the first tunnel member 110 on the lateral surface of the greater tuberosity 200 of the humerus approximately 30 mm inferior to the superior border of the tuberosity. The guide 100 is oriented such that it is perpendicular to the long axis of the humerus and perpendicular to the acromion (not shown).

Figure 19:
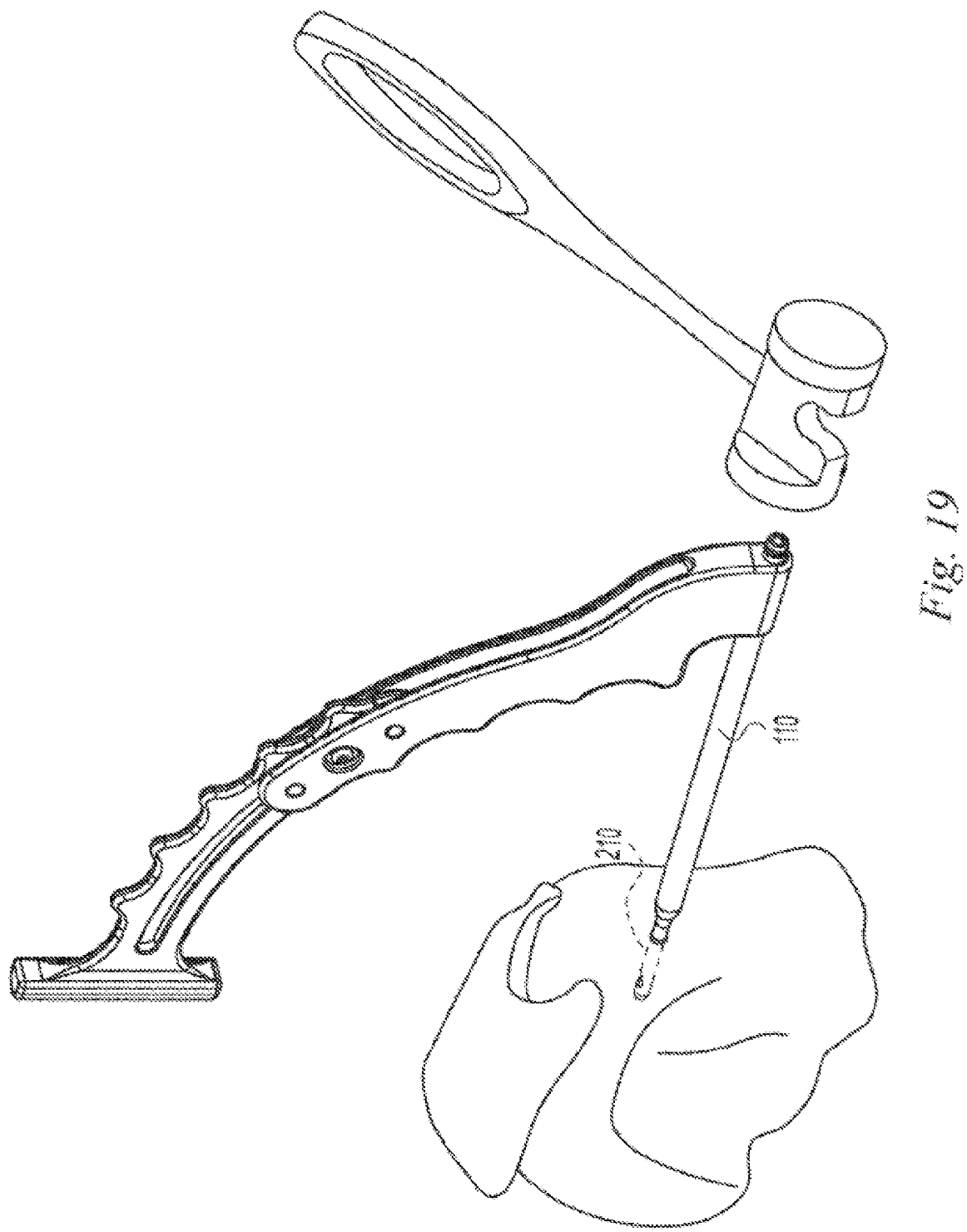

Referring to FIG. 19, the first tunnel member 110 is impacted into the bone to form a first, or lateral, bone tunnel 210.

Figure 20:
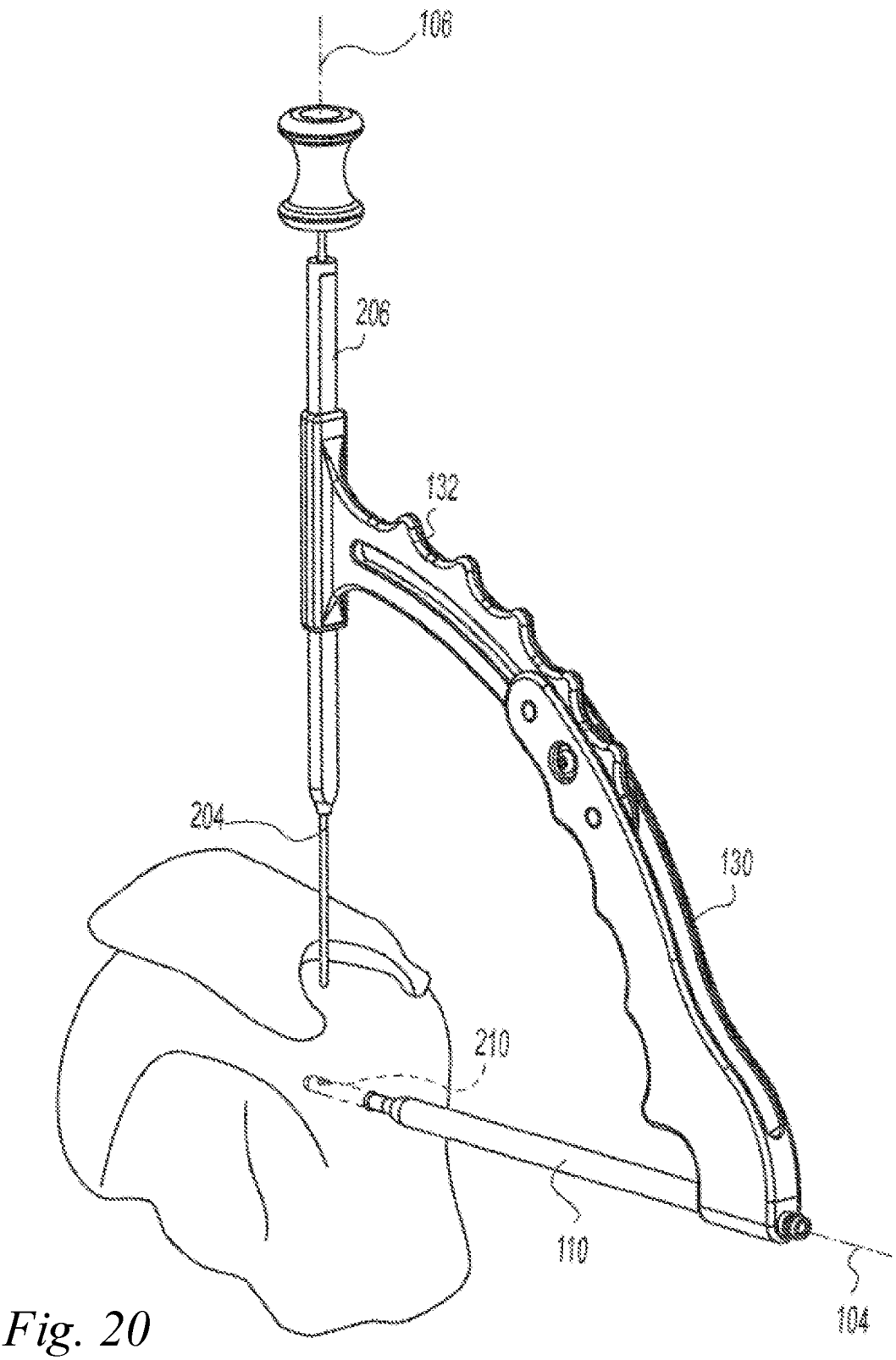

Referring to FIG. 20, the location for a second, or medial, tunnel is visualized using a targeting wire 204 in a targeting sleeve 206 to constrain the wire 204 to translation along the second guide axis 106. The position of the targeting wire may be adjusted in two degrees of freedom. First, the guide 100 may be rotated about the first guide axis 104 by twisting the first tunnel member 110 in the lateral bone tunnel 210. Second, the guide may be repositioned by adjusting the first and second arc members 130, 132 to change the angle between the guide axes 104, 106 (or repositioning the targeting sleeve and targeting wire in a different receiver in a unitary guide such as that of FIG. 9). As these adjustments are made, the targeting wire 204 may be inserted through the skin and other soft tissues near the targeted site so that the position may be visualized on the bone. The small punctures in the skin and other soft tissues created by the targeting wire 204 cause minimal trauma to the tissues and facilitate multiple targeting attempts if needed. The targeting wire 204 is then used to mark the bone surface with the desired medial tunnel location.

Figure 21:
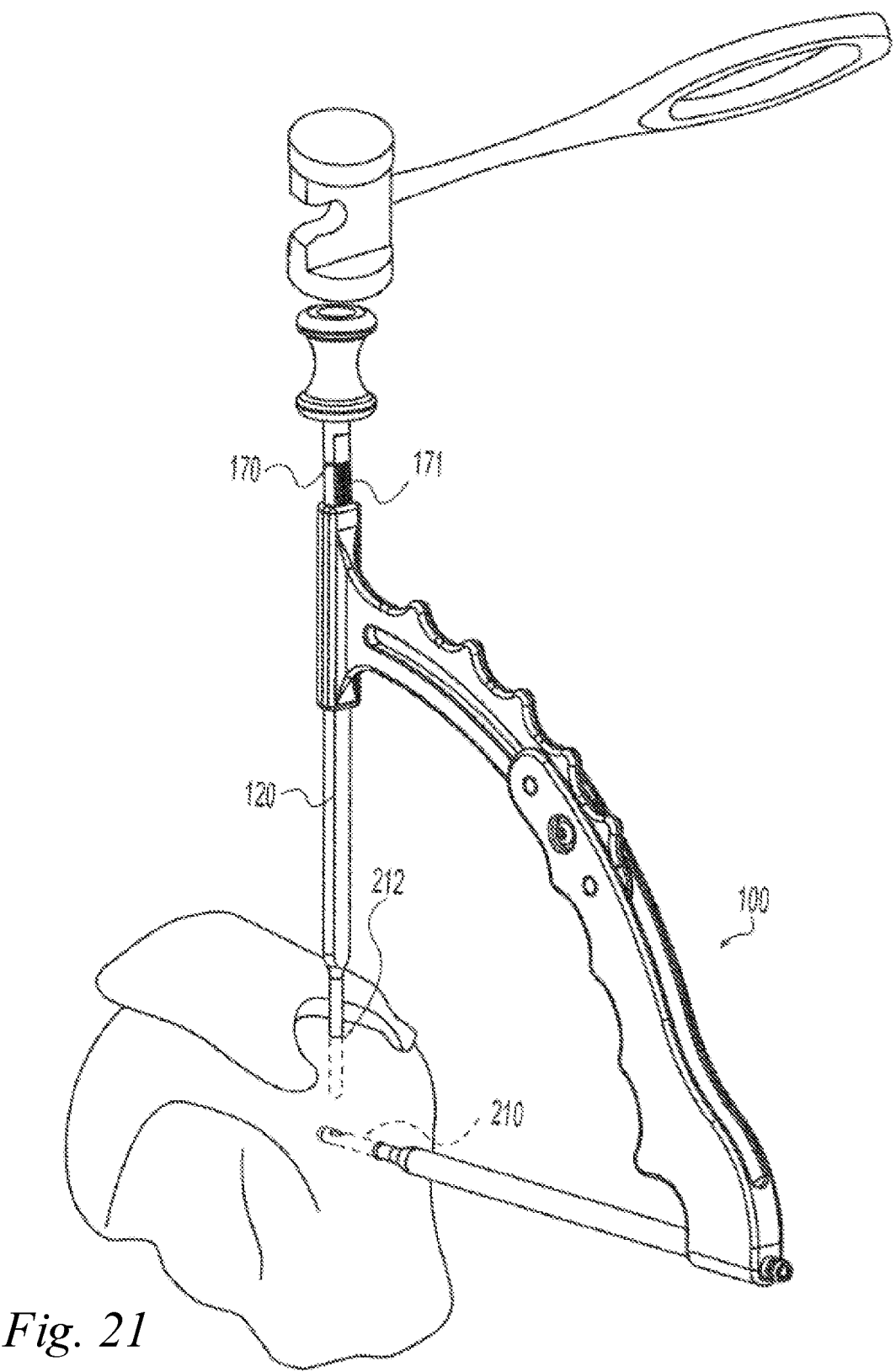

Referring to FIG. 21, the targeting sleeve and wire are removed and the second tunnel member 120 is impacted to form a second, or medial, tunnel 212.

Figure 22:
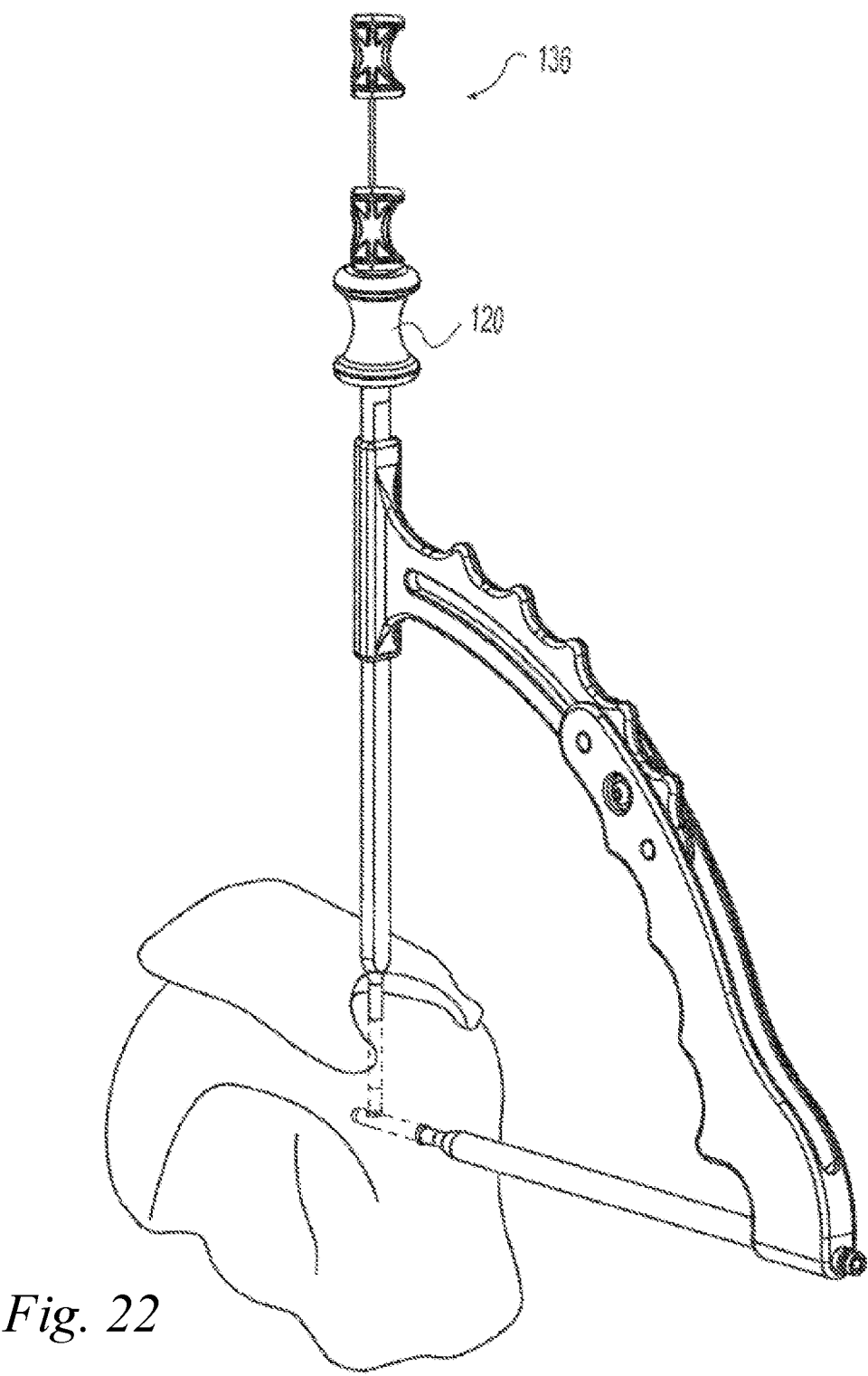

Referring to FIG. 22, the second tunnel member 120 is engaged with the first tunnel member 110 and the passer 400 inserted into the second tunnel member 120.

Figure 23:
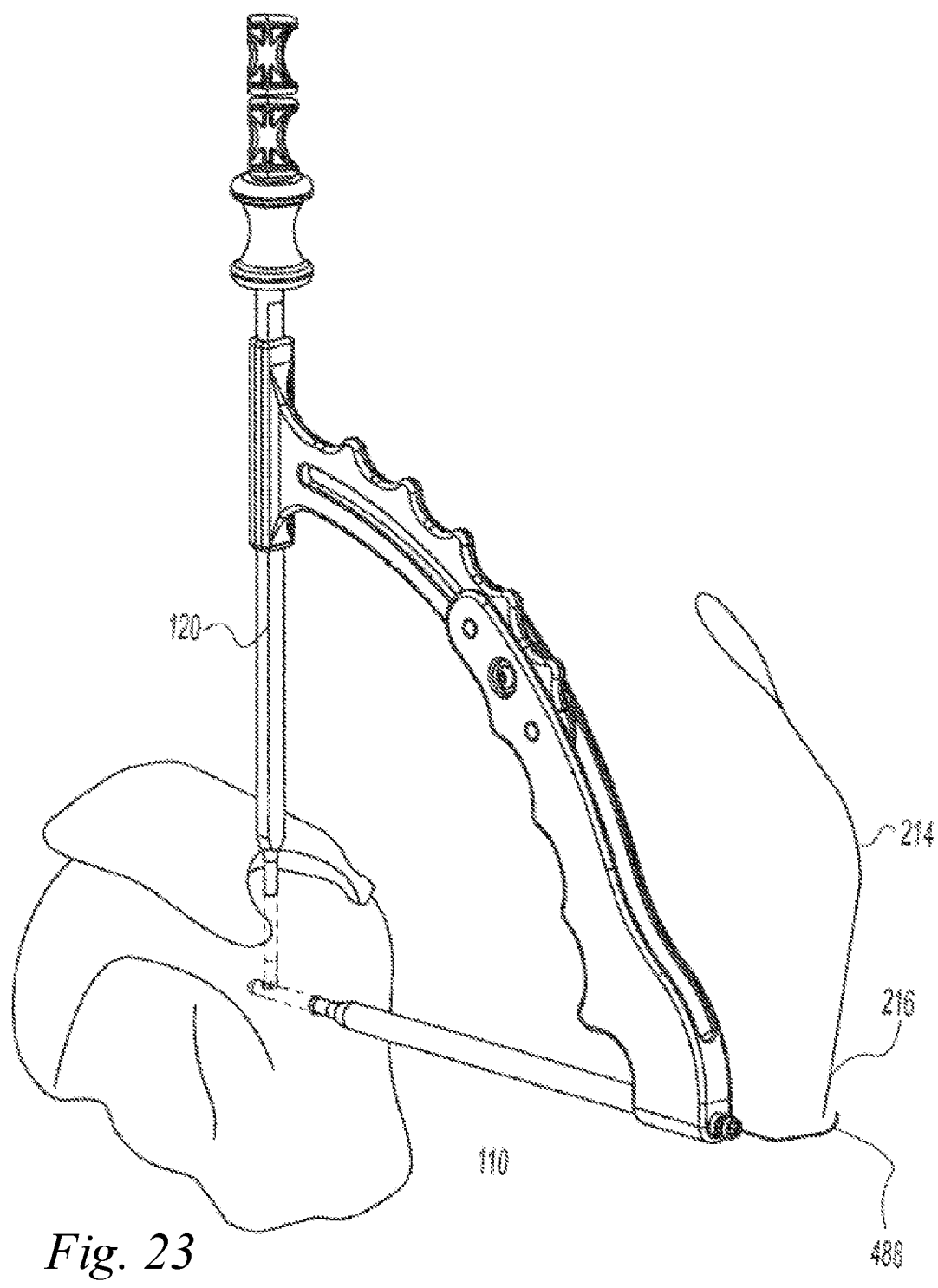

Referring to FIG. 23, the wire is advanced through the first and second tunnel members 110, 120 until it extends from the proximal end of the first tunnel member 110. The end 216 of a first shuttle suture 214 is passed through the loop 488 of the passer 400.

Figure 24:
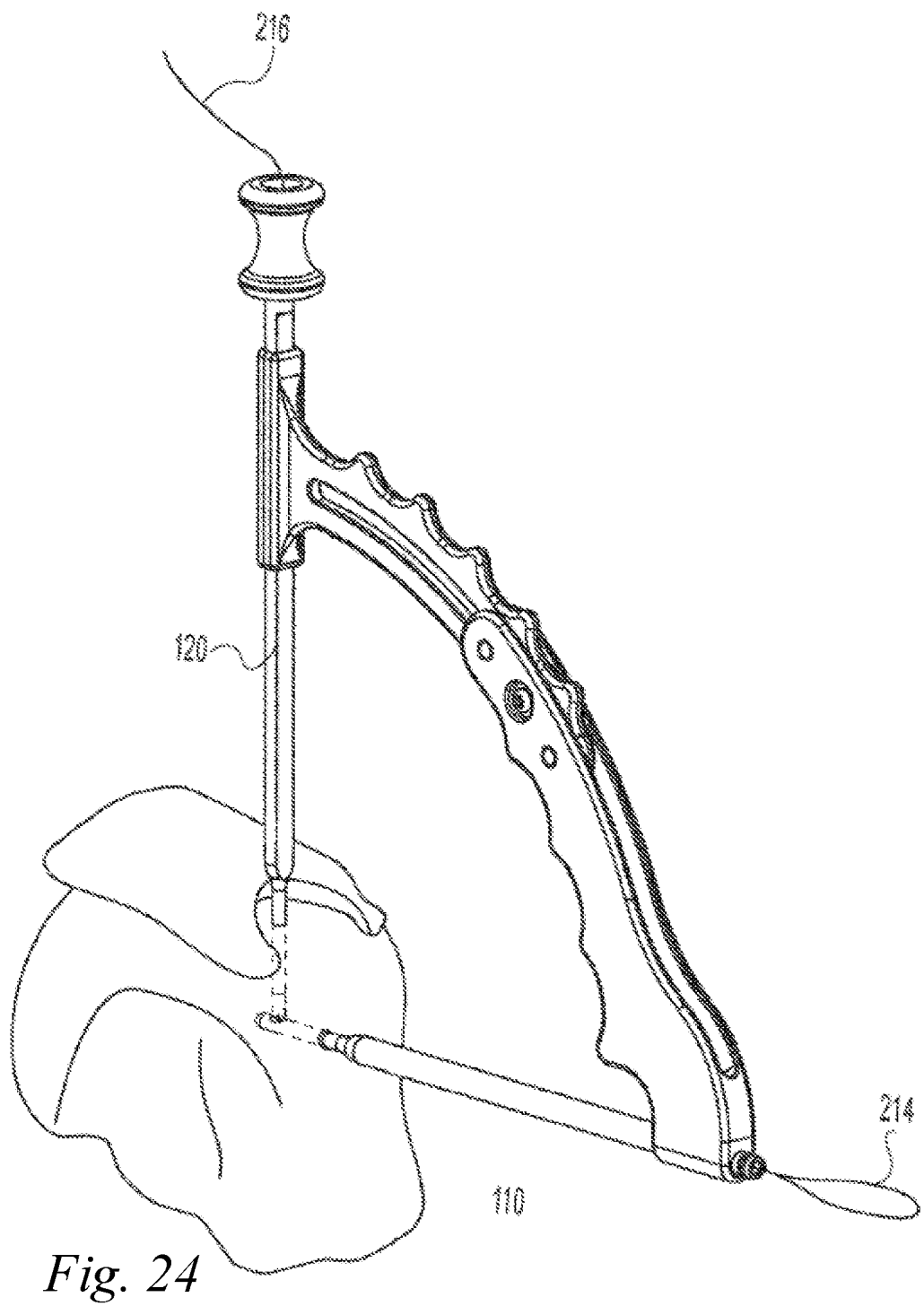

Referring to FIG. 24, the end 216 of the shuttle suture 214 is retrieved by pulling the passer 136 out the distal end of the second tunnel member 120.

Figure 25:
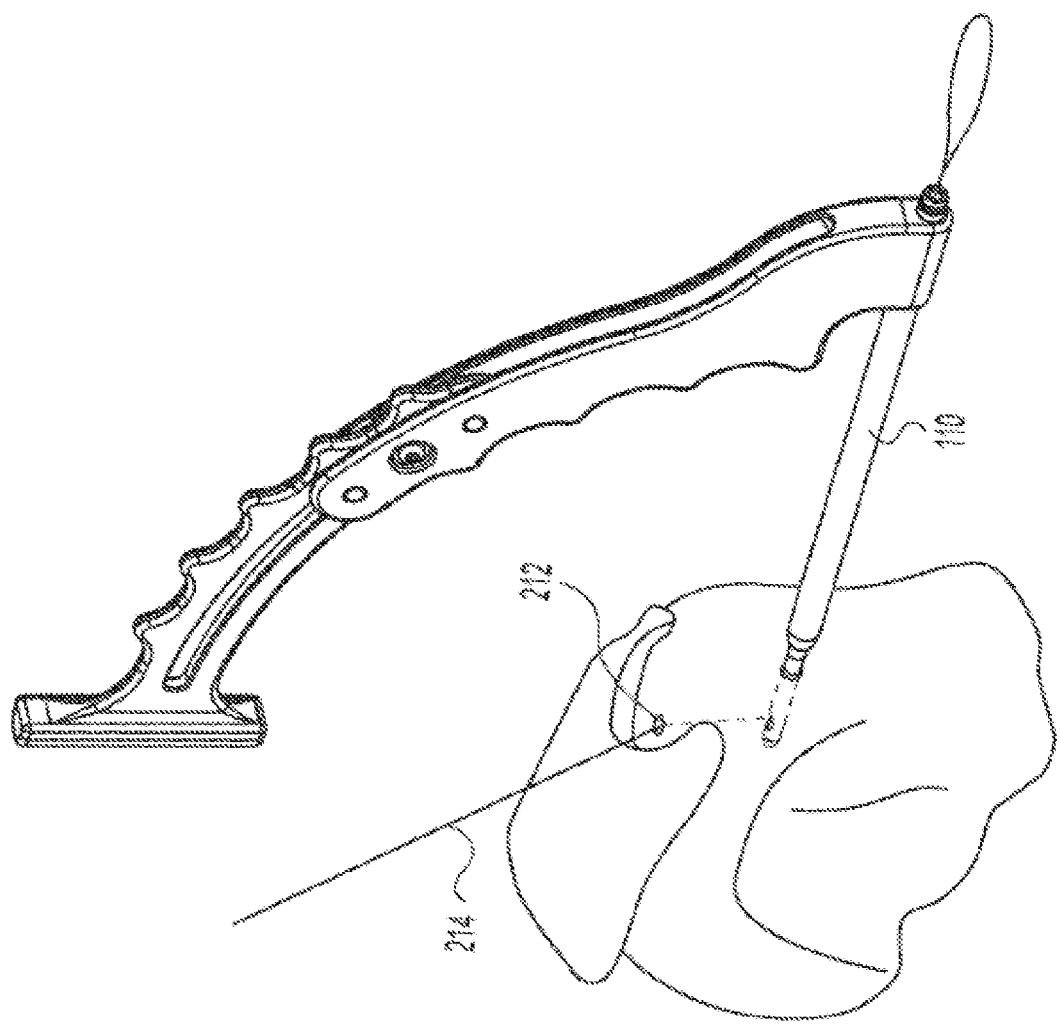

Referring to FIG. 25, the second tunnel member 120 is removed leaving the first shuttle suture 214 in place in the first tunnel member 110 and extending out of the second, medial bone tunnel 212.

Figure 26:
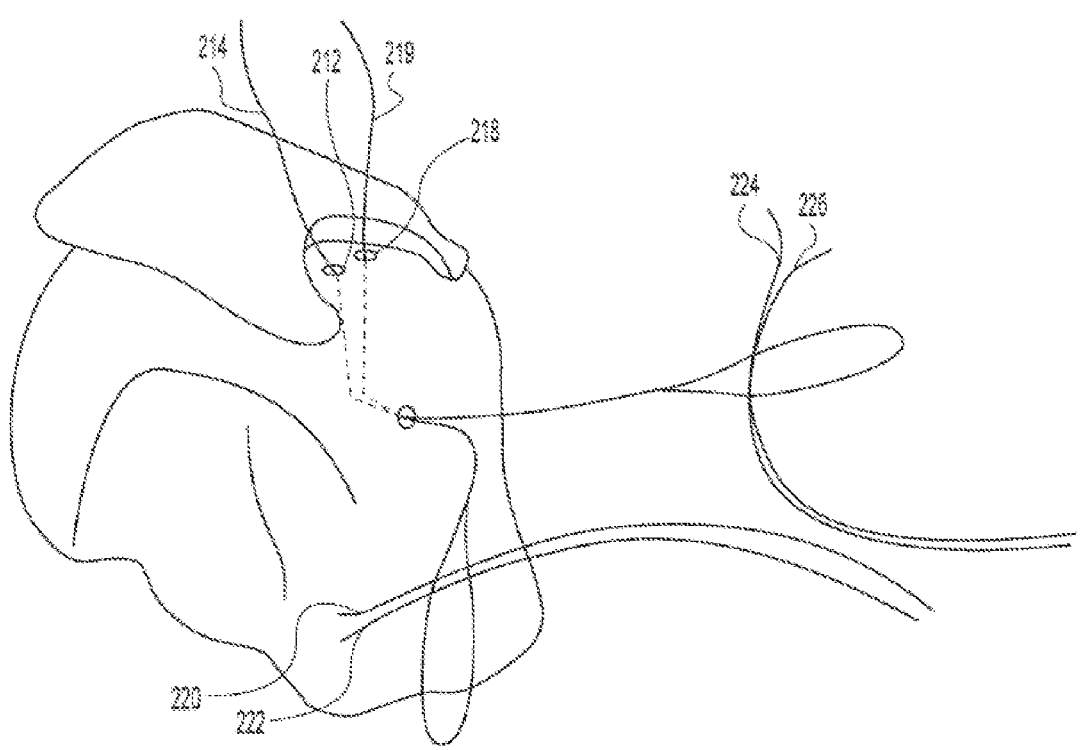
Figure 27:
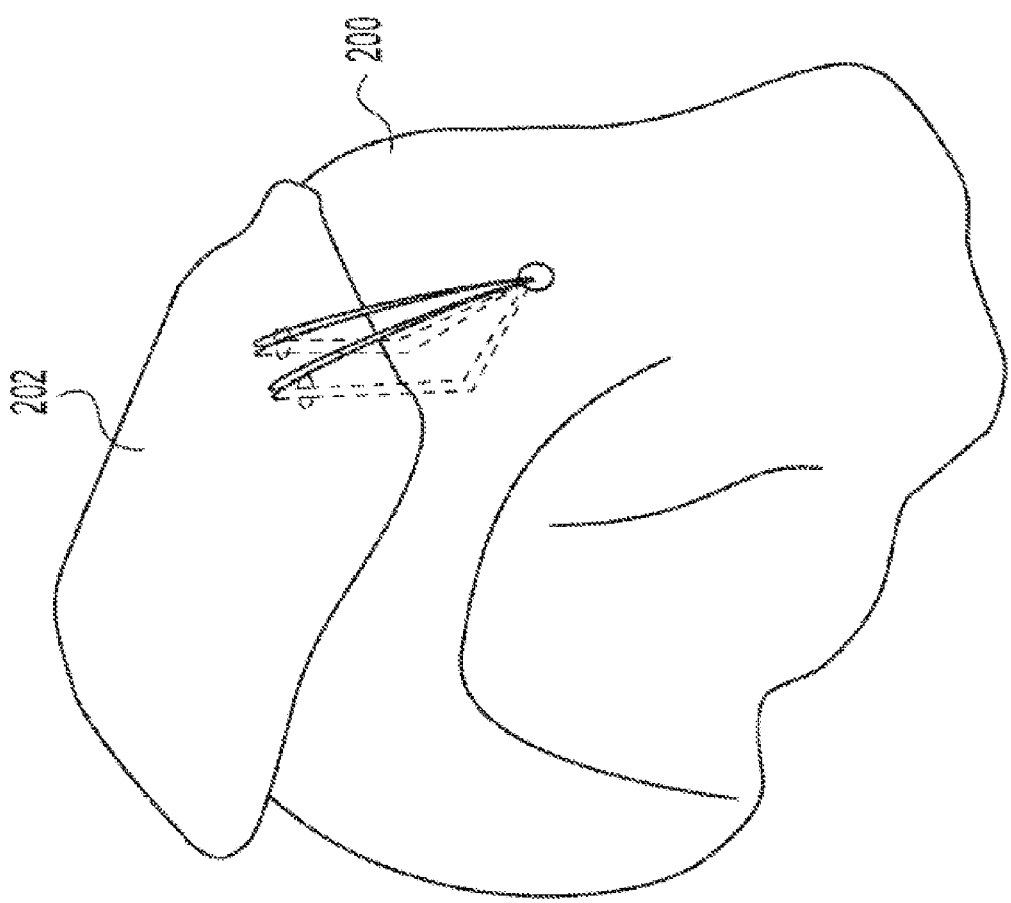

Referring to FIGS. 26 and 27, the preceding steps are repeated to create a third, additional medial, tunnel 218 and place a second shuttle suture 219 while the first tunnel member 110 remains in the bone and while the first shuttle suture 214 remains in the first tunnel member 110. Two limbs 220, 222 of a first repair suture are passed through the loop of the first shuttle suture 214 and two limbs 224, 226 of a second repair suture are passed through the loop of the second shuttle suture 219. The shuttle sutures 214, 219 are pulled to pass the limbs of the repair sutures through the bone. The repair sutures are passed through the rotator cuff 202 and used to secure it to the humerus 200.

Figure 28:
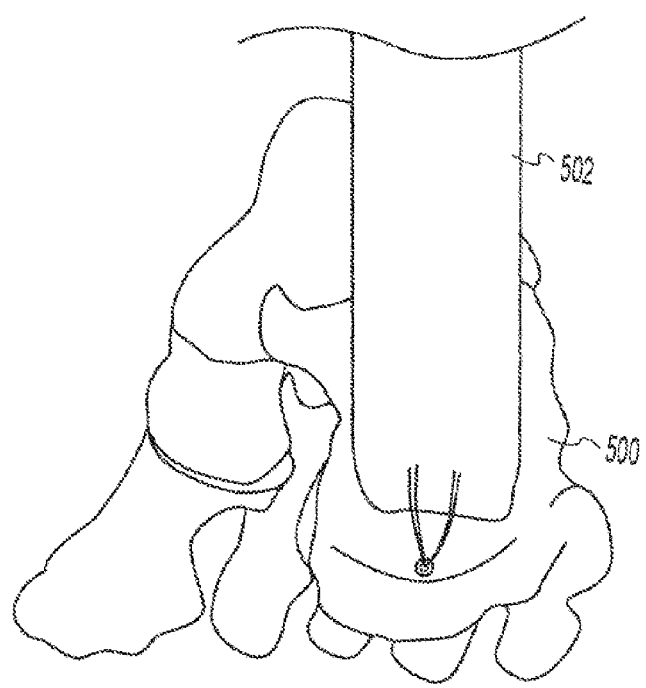
Figure 29A:
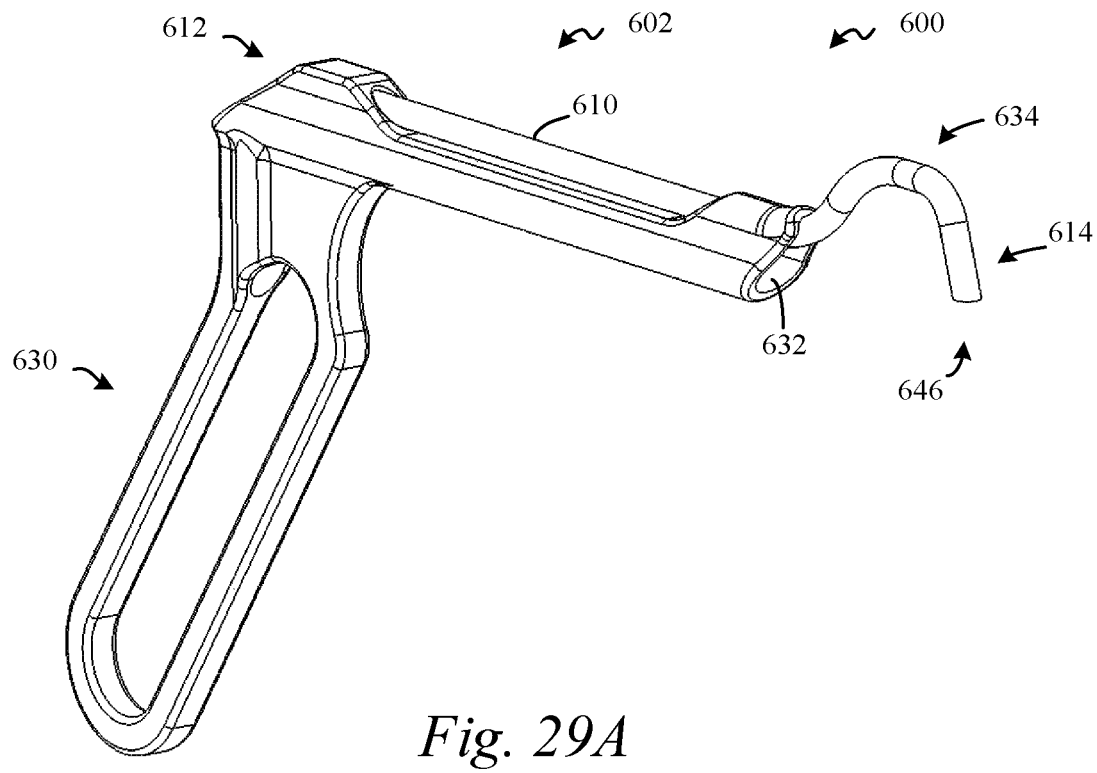
FIGS. 29A and 29B are perspective views of another example guide body of the present disclosure.
Figure 29B:
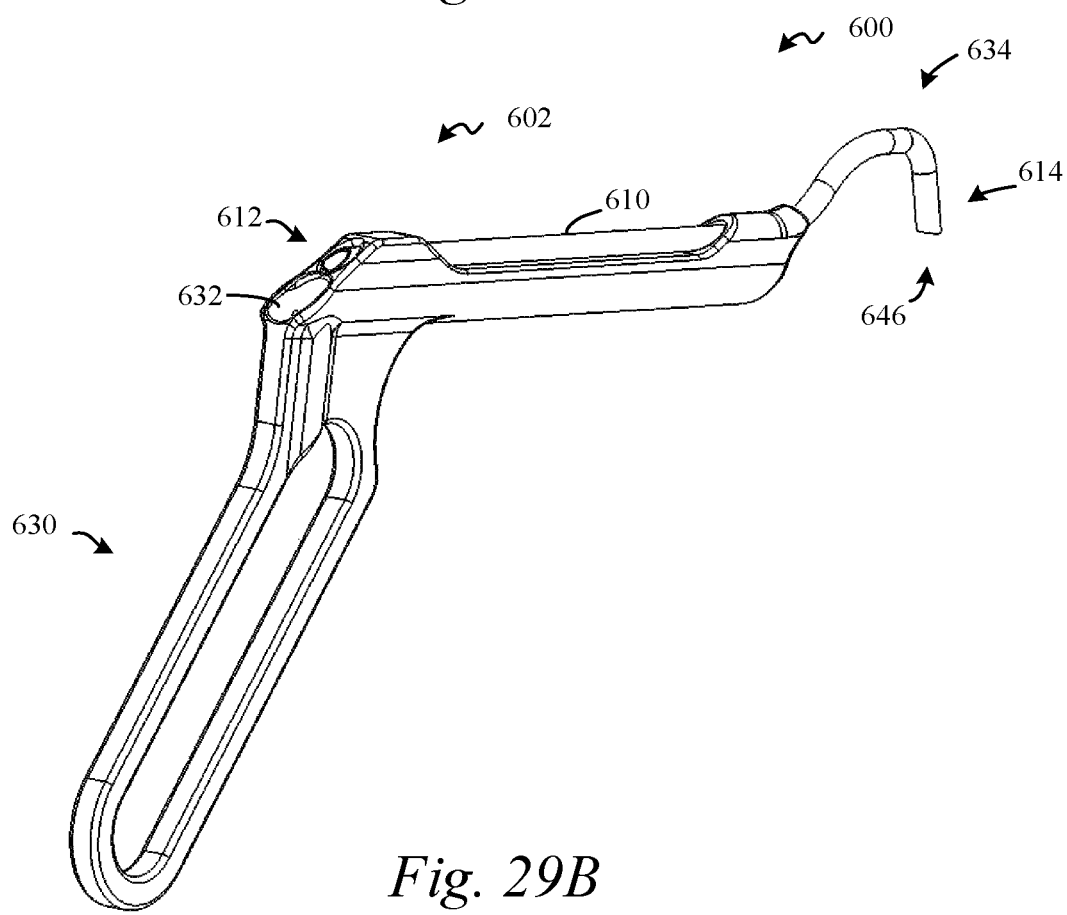
Figure 30A:
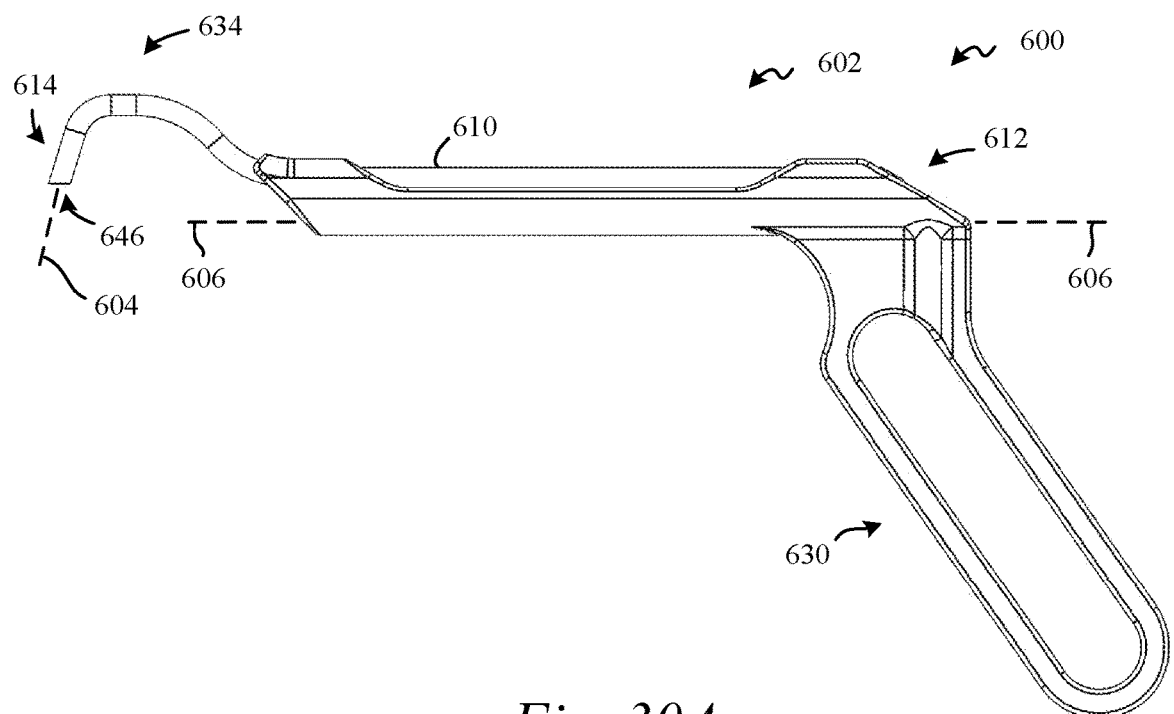
FIG. 30A is a side elevation view of the guide body of FIGS. 29A and 29B.
Figure 30B:
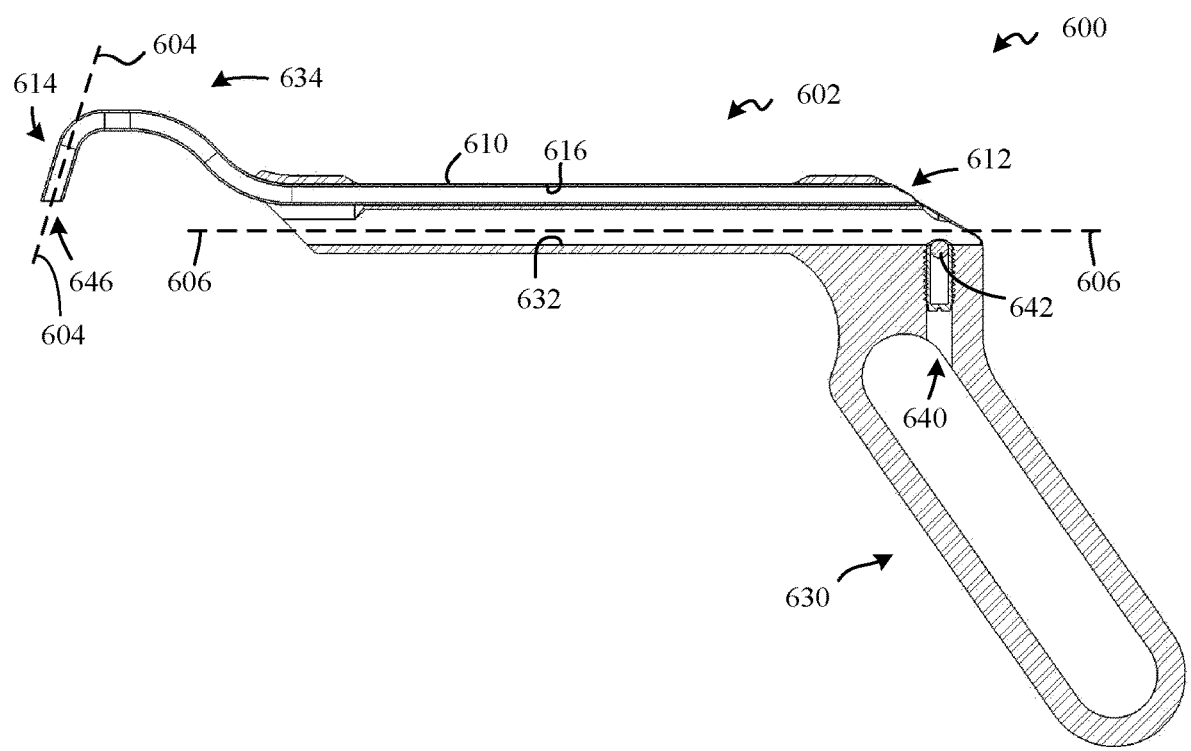
FIG. 30B is a side section view of the guide body of FIG. 30A.

Referring to FIG. 28 the instruments and methods may also be used for other repairs such as, for example, an Achilles tendon repair in which the first and second tunnel members are inserted into the heel bone 500 and one or more sutures are passed and used to secure the Achilles tendon 502 to the bone 500.

While the illustrative examples have shown bone tunnels being formed by punching instruments into the bone, it is also within the scope of the present disclosure to form bone tunnels by drilling, reaming, broaching, and/or any suitable tunnel forming process. It is contemplated, and within the scope of the present disclosure, that the various features of the illustrative examples may be interchanged among the illustrative examples.

FIGS. 29A-31C depict another example surgical instrument or guide 600 that may be used place a flexible member transosseously through first and second bone tunnels oriented transverse to each other and intersecting one other at a location within a bone. FIGS. 32-39 depict methods for placing a flexible member transosseously through first and second transverse, intersecting bone tunnels utilizing the guide 600 shown in FIGS. 29A-31C.

Referring now to FIGS. 29A-30B, the guide 600 may include a guide body 602. The guide body 602 may include a first tunnel member 610, a longitudinal guide body passage 632 (FIG. 30B), a guide body handle portion 630, and a detent mechanism 640.

The first tunnel member 610 may be engaged with the guide body 602 in a fixed fashion, or in a removably engaged fashion, and may include a proximal end 612, a distal end 614, a distal opening 646, a curved portion 634 that is nearer the distal end 614 than the proximal end 612 of the first tunnel member 610, and a first longitudinal passage 616 (FIG. 30B) that extends through the first tunnel member 610 and communicates with the distal opening 646. In one embodiment, the curved portion 634 may include a first bend 631, a second bend 633, a third bend 635, a first straight segment 636 and a second straight segment 637. However, in other embodiments (not shown) the curved portion 634 may include a single continuous bend, or any number of bends and/or any number of straight segments, without departing from the spirit or scope of the present disclosure. The distal end 614 of the first tunnel member 610 may define a first guide axis 604 and at least a portion of the first longitudinal passage 616, near the distal end 614 of the first tunnel member 610, may be coaxial with the first guide axis 604.

The longitudinal guide body passage 632 may be formed in the guide body 602 and may define a second guide axis 606. The first guide axis 604 and the second guide axis may be configured to intersect each other at a location spaced from the guide body 602 and at least a portion of the first longitudinal passage 616 near the proximal end 612 of the first tunnel member 610 may be parallel with the second guide axis 606 and/or parallel with the longitudinal guide body passage 632.

The detent mechanism 640 may be formed in the guide body handle portion 630 and may include a spring-biased ball plunger 642 that protrudes into the longitudinal guide body passage 632, as will be explained in more detail below.

Figure 31A:
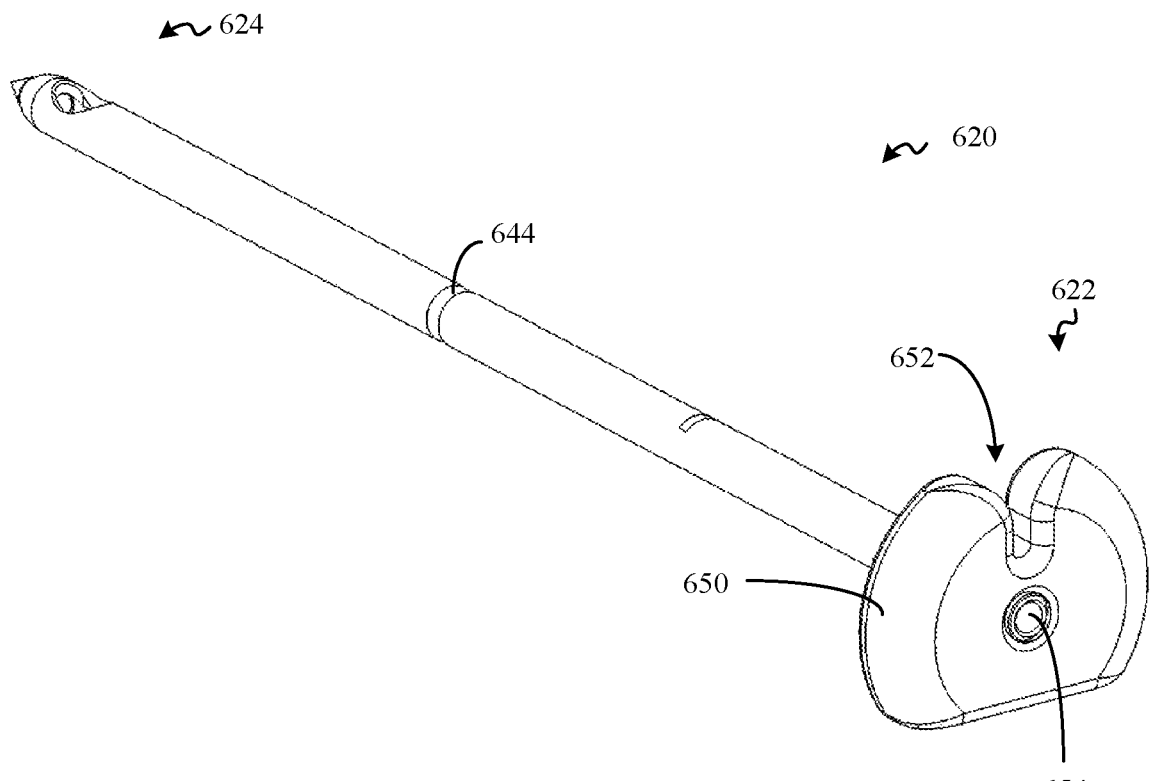
FIG. 31A is a perspective view of an example second tunnel member that may be used with the guide of FIGS. 29A-30B.
Figure 31B:
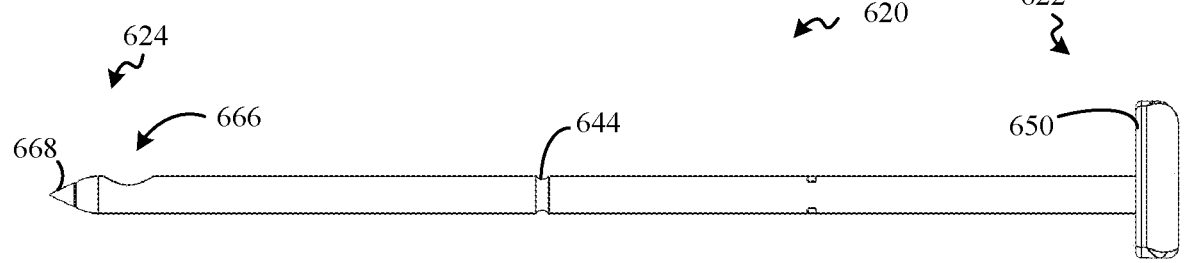
FIG. 31B is a side elevation view of the second tunnel member of FIG. 31A.
Figure 31C:
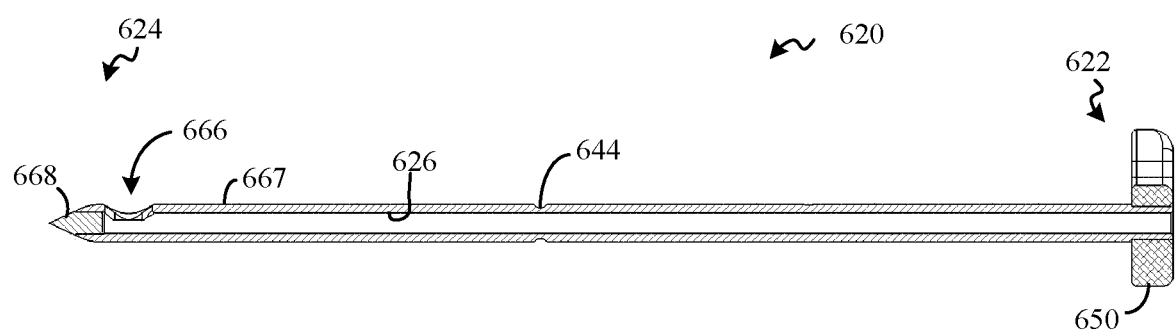
FIG. 31C is a side section view of the second tunnel member of FIG. 31B.

Referring now to FIGS. 31A-31C, the guide 600 may include a second tunnel member 620. In at least one embodiment, the second tunnel member 620 may be a bone punch that is removably engaged with the longitudinal guide body passage 632. In this manner, the second tunnel member 620 may be separable from the guide body 602 and may engage the guide body 602 in an axial sliding relationship along the second guide axis 606 within the longitudinal guide body passage 632. The second tunnel member 620 may include a proximal end 622, a distal end 624, a second longitudinal passage 626, a side wall 667, a side opening 666, a sharp point 668, an annular notch 644, a handle 650, a first aperture 652 formed in the handle 650, and a second aperture 654 formed in the handle 650.

The second longitudinal passage 626 may extend at least partway through the second tunnel member 620 and the second longitudinal passage 626 may be coaxial with the second guide axis 606 when the second tunnel member 620 is engaged within the longitudinal guide body passage 632.

As previously discussed, the detent mechanism 640 may be configured to engage and retain the second tunnel member 620 in a desired axial position relative to the guide body 602, causing the second tunnel member 620 to resist axial movement along the second guide axis 606. The annular notch 644 that is formed in the side wall 667 of the second tunnel member 620 may have a complementary shape that interacts with the spring-biased ball plunger 642 of the detent mechanism 640 to resist axial sliding of the second tunnel member 620 within the longitudinal guide body passage 632. This feature may help prevent the second tunnel member 620 from accidentally falling out of the longitudinal guide body passage 632 as the guide 600 is moved about during surgical procedures. The spring-biased ball plunger 642 may achieve this function by engaging within the annular notch 644 and resisting axial sliding of the second tunnel member 620 due to a spring-biased forced that is placed upon the ball plunger. However, the surgeon can still freely rotate the second tunnel member 620 within the longitudinal guide body passage 632 because the spring-biased ball plunger 642 will remain within the annular notch 644 as the second tunnel member 620 is rotated within the longitudinal guide body passage 632. Moreover, sufficient axial force may be applied to the second tunnel member 620 to overcome the force of the spring-biased ball plunger 642 and eject the spring-biased ball plunger 642 from within the annular notch 644 and freely slide the second tunnel member 620 axially within longitudinal guide body passage 632.

The side opening 666 may be formed in the side wall 667 nearer the distal end 624 of the second tunnel member 620 than the proximal end 622 of the second tunnel member 620. The second longitudinal passage 626 may extend from the proximal end 622 of the second tunnel member 620 toward the distal end 624 of the second tunnel member 620 and may communicate with the side opening 666. The side opening 666 formed in the second tunnel member 620, and the distal opening 646 of the first tunnel member 610, may be in communication with each other when the second tunnel member 620 is axially translated such that the first guide axis 604 intersects the side opening 666 of the second tunnel member 620.

Figure 35:
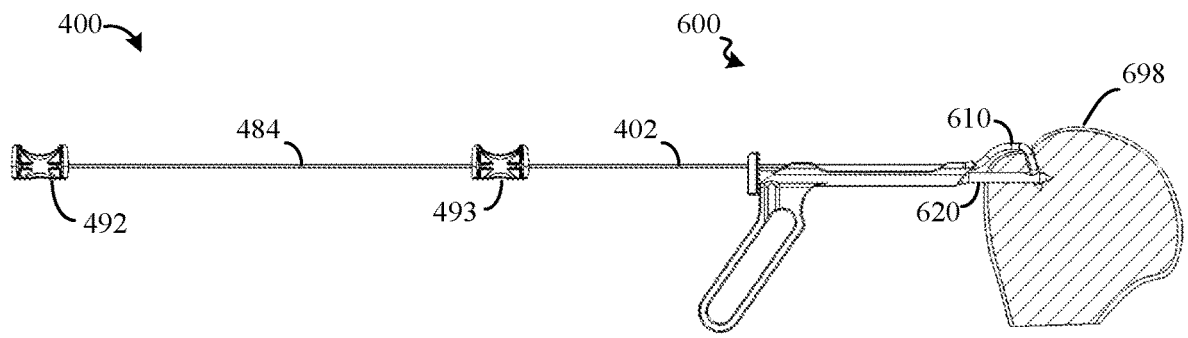
FIG. 35 is a side elevation view of the guide of FIGS. 29A-31C engaged with the bone of FIG. 32 and a passer inserted into the first tunnel member.
Figure 36:
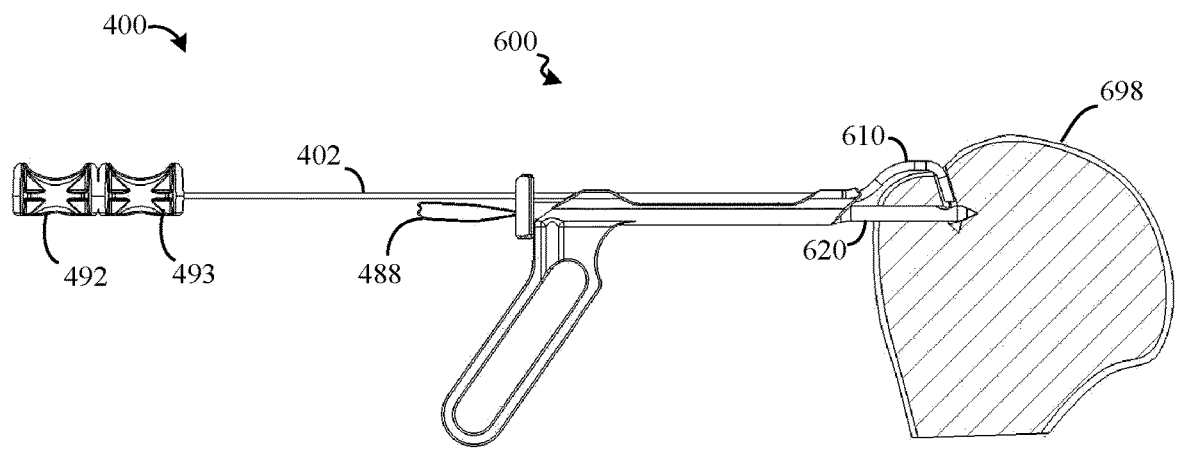
FIG. 36 is a side elevation view of the guide of FIGS. 29A-31C engaged with the bone of FIG. 32 with a passer wire threaded through both tunnel members and protruding from the proximal end of the second tunnel member.
Figure 37:
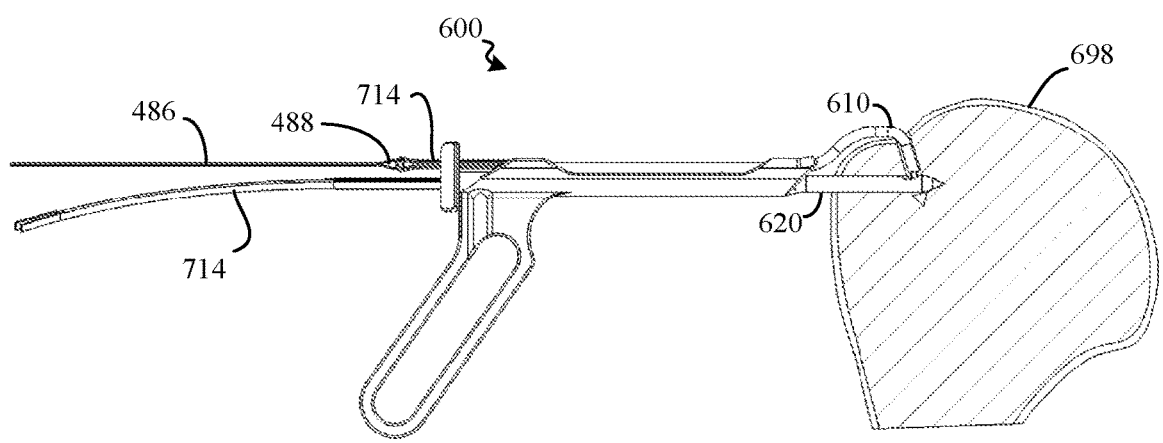
FIG. 37 is a side elevation view of the guide of FIGS. 29A-31C engaged with the bone of FIG. 32 with a first flexible member engaged with the passer wire and pulled through both tunnel members.

FIGS. 35-37 show how the guide 600 may be used with a passer, such as the passer 400 shown in FIGS. 12-13. The passer 400 may be operable to extend from the proximal end 612 of the first tunnel member 610, through the distal end 614 of the first tunnel member 610, through the distal end 624 of the second tunnel member 620, and to the proximal end 622 of the second tunnel member 620 in one continuous path. The passer 400 may then be used to pull a flexible member 714 such as, for example, a passing suture or a repair suture through the tunnel members 610, 620 to pass the flexible member 714 through the bone 698.

FIGS. 32-38 illustrate an example of a surgical method according to the present disclosure. In the illustrative example of FIGS. 32-38, instruments and methods of the previous examples are shown in use to place transosseous sutures to repair a rotator cuff of a shoulder joint. However, it will be understood that any of the examples of instruments and methods of the present disclosure may be used in any combination to pass a member through a shoulder bone or other bones at a shoulder or other surgical sites and for rotator cuff repair and/or other surgical purposes.

Figure 32:
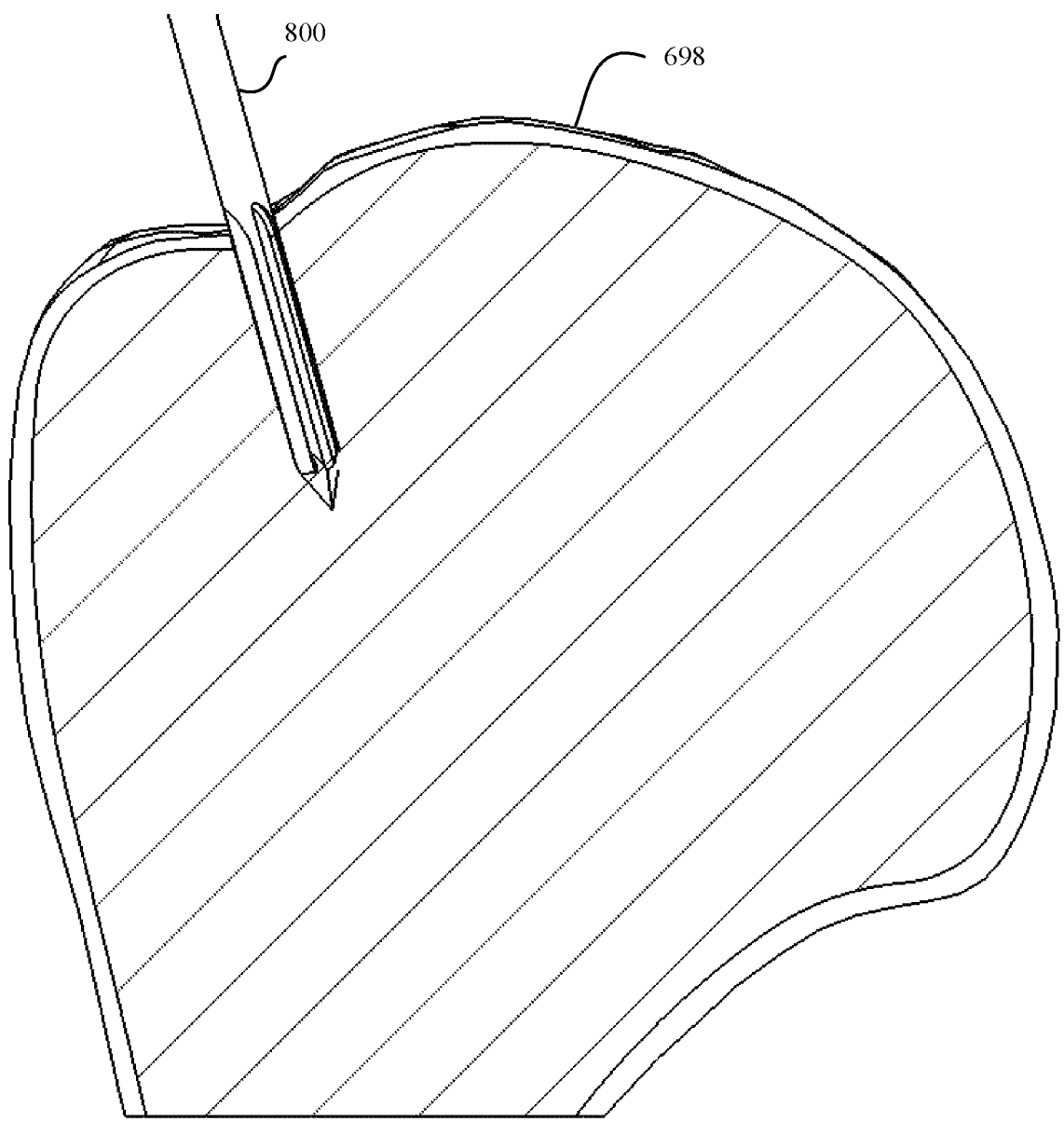
FIG. 32 is a side section view of a bone with a punch inserted into the bone to form a first bone tunnel.

Referring to FIG. 32, a tool 800, such as a medial bone punch, a bone drill, etc., may be used to form a first bone tunnel in the bone 698.

Figure 33:
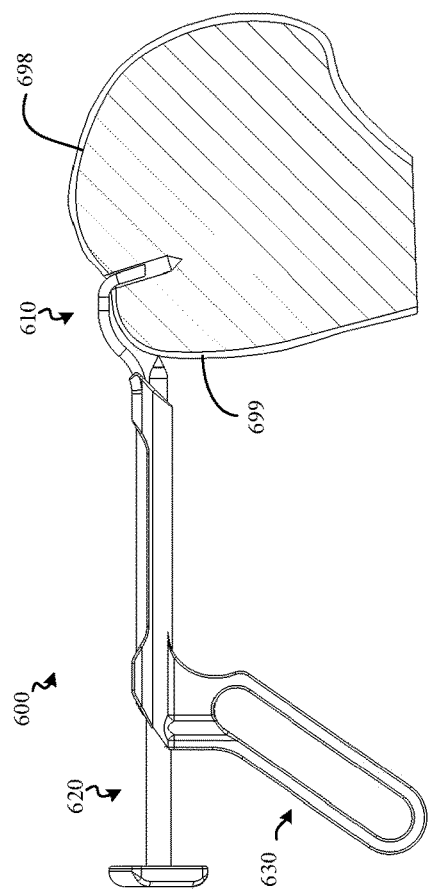
FIG. 33 is a side elevation view of the guide of FIGS. 29A-31C engaged with the bone of FIG. 32 and a first tunnel member inserted into the first bone tunnel.

Referring to FIG. 33, the guide 600 may be placed proximal the bone 698 with the distal end 614 of the first tunnel member 610 inserted into the first bone tunnel that was formed by the tool 800 in FIG. 33. The guide 600 may be rotated back and forth, and pitched up and down, while the first tunnel member 610 is inserted into the first bone tunnel to position the sharp point 668 of the second tunnel member 620 at the desired location on the surface of the bone 698 before punching the second bone tunnel into the bone 698 using the second tunnel member 620. For example, the desired location of the sharp point 668 of the first tunnel member 110 on the surface of the bone 698 may be on the lateral surface of the greater tuberosity 699 of the humerus approximately 30 mm inferior to the superior border of the tuberosity. The guide 600 may be oriented such that it is perpendicular to the long axis of the humerus and perpendicular to the acromion (not shown).

Figure 34:
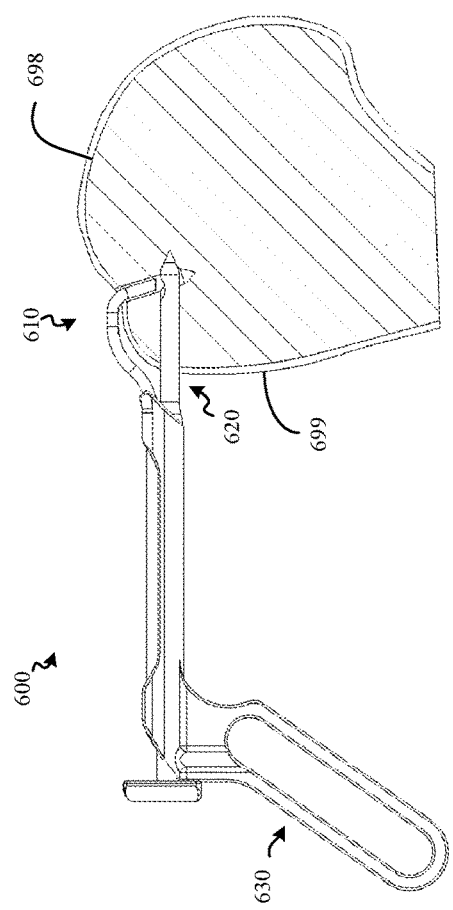
FIG. 34 is a side elevation view of the guide of FIGS. 29A-31C engaged with the bone of FIG. 32 and the second tunnel member inserted into the bone.

Referring to FIG. 34, the second tunnel member 620 may be impacted into the bone 698 to form the second bone tunnel. The second tunnel member 620 may also be rotated/oriented to engage the distal opening 646 of the first tunnel member 610 with the side opening 666 of the second tunnel member 620, such that the distal opening 646 of the first tunnel member 610 and the side opening 666 of the second tunnel member 620 are in communication with each other.

Referring to FIG. 35, the passer 400 may be inserted into the proximal end 612 of the first tunnel member 610.

Referring to FIG. 36, the wire 486 of the passer 400 may be advanced through the first tunnel member 610, into the second tunnel member 620, and then further advanced until the bent loop 488 on the end of the wire 486 protrudes from the proximal end 622 of the second tunnel member 620.

Referring to FIG. 37, the first flexible member 714 may be passed through the bent loop 488 of the wire 486, to engage the first flexible member 714 with the passer 400, and the first flexible member 714 may then be threaded through the tunnel members 610, 620 (and the bone tunnels) by pulling the wire 486 out of the proximal end 612 of the first tunnel member 610.

Figure 38:
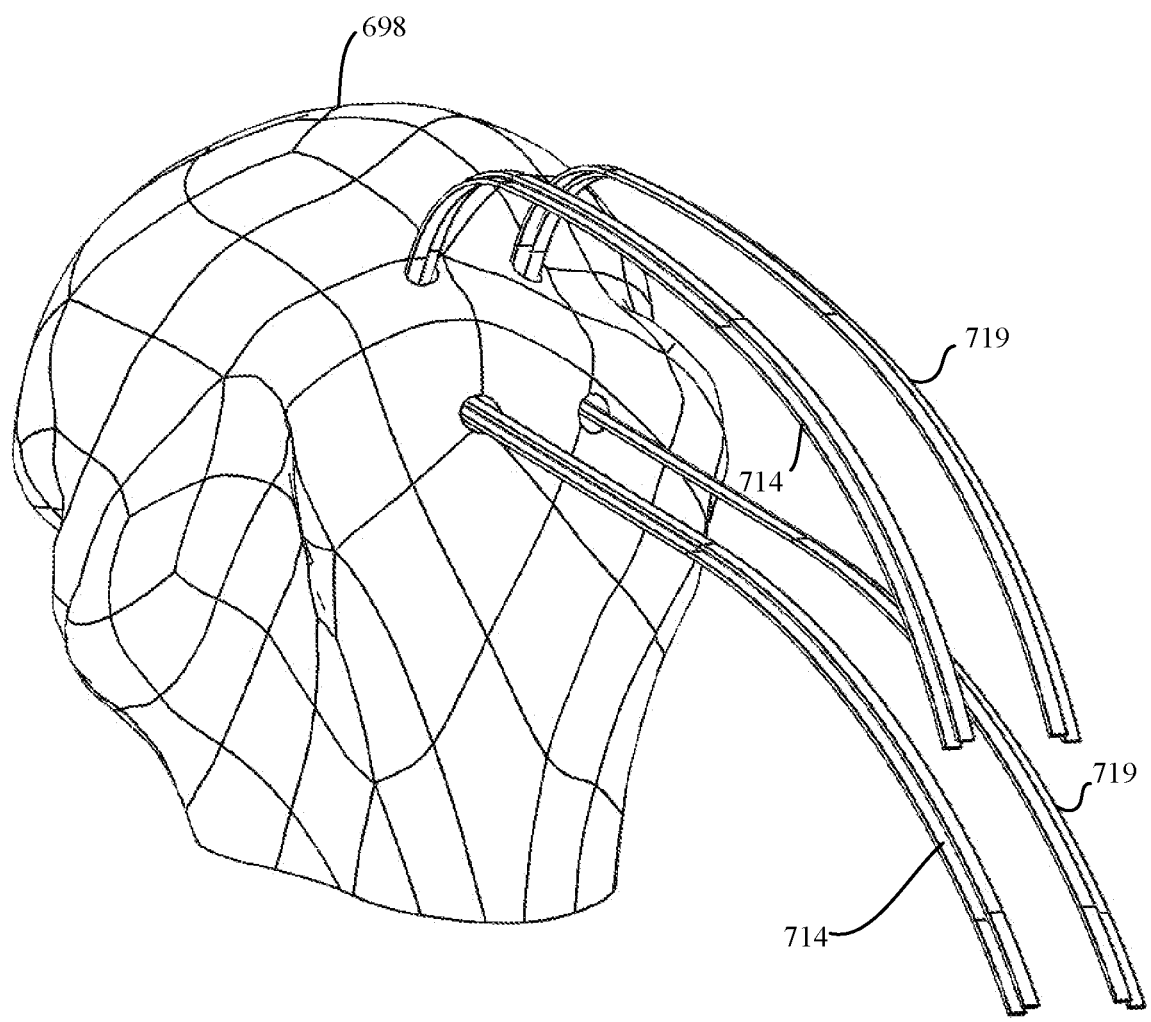
FIG. 38 is a perspective view of a bone with first and second flexible members passed through the bone.

Referring to FIG. 38, the first tunnel member 610 and the second tunnel member 620 are removed from the bone tunnels, along with the guide 600, leaving the first flexible member 714 in place in the bone 698. Moreover, the preceding steps may be repeated to create additional bone tunnels and place a second flexible member 719 (or more flexible members, as desired), as shown in FIG. 38.

Figure 39:
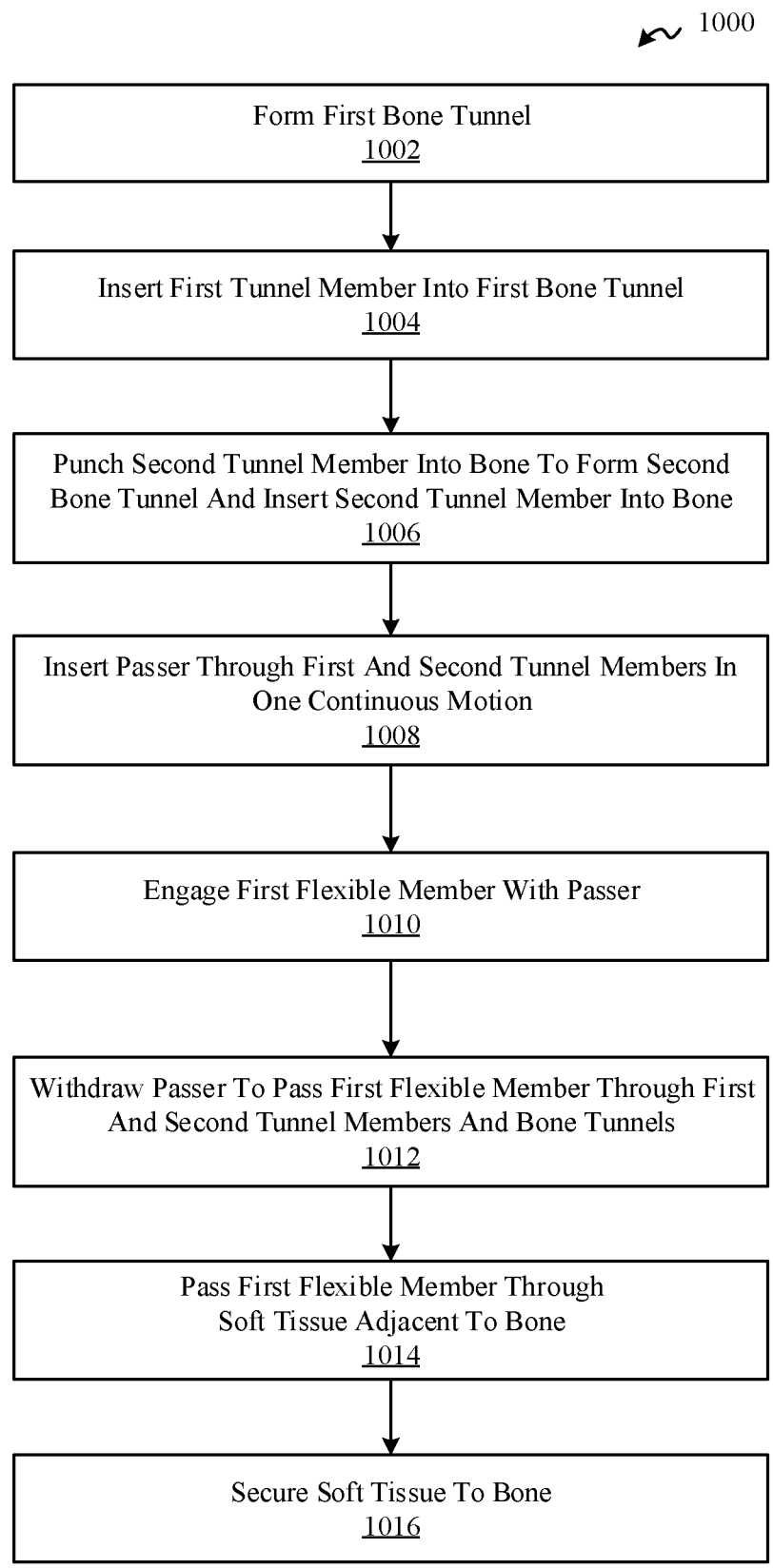
FIG. 39 is a flowchart diagram illustrating a method of placing a flexible member transosseously through first and second transverse, intersecting bone tunnels.

Referring now to FIG. 39, a flowchart diagram is shown of a method 1000 of placing a flexible member transosseously through first and second transverse, intersecting bone tunnels, according to embodiments of the present disclosure. The method 1000 may be carried out through the use of any of the surgical instruments of FIGS. 1-37. Alternatively, the method 1000 may be carried out with surgical instruments different from those shown in FIGS. 1-37 and/or described elsewhere herein.

The method 1000 may begin with a step 1002, in which a first bone tunnel may be formed in a bone 698. The first bone tunnel may be sized and configured to receive a first tunnel member 610 therein.

The method 1000 may then proceed to a step 1004, in which a first tunnel member 610 may be inserted into the first bone tunnel of the bone 698 along a first insertion axis 604. The first tunnel member 610 may include a proximal end 612, a distal end 614, and a first longitudinal passage 616 extending through the first tunnel member 610.

The method 1000 may then proceed to a step 1006, in which a second tunnel member 620 may be inserted into the bone 698 along a second insertion axis 606 and the second insertion axis 606 may intersect the first insertion axis 604. The second tunnel member 620 may be punched into the bone 698 to form a second bone tunnel and insert the second tunnel member 620 into the bone 698 along the second insertion axis 606 after the first tunnel member 610 has been inserted into the first bone tunnel. The second tunnel member 620 may include a proximal end 622, a distal end 624, and a second longitudinal passage 626 extending at least partway through the second tunnel member 620.

The method 1000 may then proceed to a step 1008, in which a passer 400 may be inserted through the first and second tunnel members 610, 620 in one continuous motion until the passer 400 extends through the first longitudinal passage 616, the second longitudinal passage 626, out of the proximal end 612 of the first tunnel member 610, and out of the proximal end 622 of the second tunnel member 620.

In other words, the passer 400 may be inserted through the first and second tunnel members 610, 620 by inserting the passer 400 so that it extends between the proximal end 612 of the first longitudinal passage 616, the distal end 614 of the first longitudinal passage 616, the distal end 624 of the second longitudinal passage 626, and the proximal end 622 of the second longitudinal passage 626 by advancing the passer 400 into the proximal end 612 of the first tunnel member 610, along the first longitudinal passage 616, through a distal opening 646 in the first tunnel member 610, through a side opening 666 in the second tunnel member 620, along the second longitudinal passage 626, and out a proximal end 622 of the second tunnel member 620 in one continuous motion.

The passer 400 may also include a wire 486 forming a loop 488 in a first plane, the loop 488 being bent so that a portion of the loop 488 forms a curved profile in a second plane perpendicular to the first plane and an outer tube 402 that is moveable relative to the wire 486 between a first position in which the outer tube 402 encloses a portion of a length of the wire 486 and a second position in which the outer tube 402 encloses less of the length of the wire 486. The wire 486 may be inserted into the first tunnel member 610 while the outer tube 402 is positioned in the first position and the outer tube 402 may be subsequently moved to the second position to pass the loop 488 from the distal opening 646 in the first tunnel member 610 through the side opening 666 in the second tunnel member 620 and out the proximal end 622 of the second tunnel member 620.

The method 1000 may then proceed to a step 1010, in which a first flexible member 714 may be engaged with the loop 488 of the passer 400.

The method 1000 may then proceed to a step 1012, in which the passer 400 may be withdrawn from the proximal end 612 of the first tunnel member 610 to pass the first flexible member 714 through the first and second tunnel members 610, 620 and the first and second bone tunnels.

The method 1000 may then proceed to a step 1014, in which the first flexible member 714 may be passed through soft tissue (not shown) adjacent to the bone 698.

The method 1000 may then proceed to a step 1016, in which the first flexible member 714 may then be used to secure the soft tissue to the bone 698.

Alternatively, or in addition thereto, the method 1000 may proceed to a step 1018, in which the soft tissue may be secured to the bone 698 by inserting a knotless anchor (not shown) into the first bone tunnel and securing the first flexible member 714 with the knotless anchor, and the method 1000 may end.

All methods disclosed herein may be implemented in a wide variety of ways. Although the various steps of the methods disclosed herein are shown and described in a certain order, those of skill in the art will recognize that the steps of the methods disclosed herein may be executed in many different order combinations from those set forth in the descriptions of their corresponding Figures. Furthermore, some of the steps of the methods disclosed herein are optional and may be omitted and/or replaced with other steps not specifically described herein.

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the preceding detailed description of the embodiments of the apparatus, system, and method, as represented in the Figures, is not intended to limit the scope of the disclosure, as claimed, but is merely representative of exemplary embodiments of the disclosure.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 paragraph 6. It will be apparent to those having skill in the art that changes may be made to the details of the above-described embodiments without departing from the underlying principles of the disclosure.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

While specific embodiments and applications of the present disclosure have been illustrated and described, it is to be understood that the disclosure is not limited to the precise configuration and components disclosed herein. Various modifications, changes, and variations which will be apparent to those skilled in the art may be made in the arrangement, operation, and details of the methods and systems of the present disclosure disclosed herein without departing from the spirit and scope of the disclosure.

What is claimed is:

1. A method for placing a member transosseously through first and second transverse, intersecting bone tunnels, the method comprising:
   inserting a first tunnel member into a bone along a first insertion axis, the first tunnel member having a proximal end, a distal end, and a first longitudinal passage;
   inserting a second tunnel member into the bone along a second insertion axis, the second insertion axis intersecting the first insertion axis, the second tunnel member having a proximal end, a distal end, and a second longitudinal passage;
   inserting a passer through the first and second tunnel members in one continuous motion until the passer extends through the first longitudinal passage, the second longitudinal passage, out of the proximal end of the first tunnel member, and out of the proximal end of the second tunnel member;
   engaging a flexible member with the passer; and
   withdrawing the passer to pass the flexible member through the first and second tunnel members.

2. The method of claim 1 further comprising:
   forming a first bone tunnel to receive the first tunnel member;
   inserting the first tunnel member into the first bone tunnel; and
   punching the second tunnel member into the bone to form a second bone tunnel and inserting the second tunnel member into the bone along the second insertion axis after the first tunnel member has been inserted into the first bone tunnel.

3. The method of claim 1 wherein inserting the passer through the first and second tunnel members comprises inserting the passer so that it extends between the proximal end of the first longitudinal passage, the distal end of the first longitudinal passage, the distal end of the second longitudinal passage, and the proximal end of the second longitudinal passage by advancing the passer into the proximal end of the first tunnel member, along the first longitudinal passage, through a distal opening in the first tunnel member, through a side opening in the second tunnel member, along the second longitudinal passage, and out a proximal end of the second tunnel member in one continuous motion.

4. The method of claim 3, wherein the passer further comprises:
   a wire forming a loop in a first plane, the loop being bent so that a portion of the loop forms a curved profile in a second plane perpendicular to the first plane; and
   an outer tube moveable relative to the wire between a first position in which the outer tube encloses a portion of a length of the wire and a second position in which the outer tube encloses less of the length of the wire.

5. The method of claim 4 further comprising:
   inserting the wire into the first tunnel member while the outer tube is positioned in the first position and subsequently moving the outer tube to the second position;
   passing the loop from the distal opening in the first tunnel member through the side opening in the second tunnel member and out the proximal end of the second tunnel member;
   engaging the flexible member with the loop of the passer prior to the withdrawing step;
   after the withdrawing step, passing the first flexible member through soft tissue adjacent to the bone; and
   securing the soft tissue to the bone.

6. The method of claim 5 wherein the step of securing the soft tissue to the bone comprises inserting a knotless anchor into a first bone tunnel and securing the first flexible member with the knotless anchor.

7. The method of claim 6, wherein the flexible member comprises a suture.

8. The method of claim 3, wherein the second tunnel member causes the flexible to member to define a curved profile in the second tunnel member as the flexible member travels toward the first tunnel member during the step of advancing the passer.

9. The method of claim 1, wherein the step of engaging the flexible member with the passer is performed outside the bone and outside each of the first and second tunnel members.

10. The method of claim 1, wherein the step of inserting the second tunnel member comprises inserting a distal end of the second tunnel member into the first tunnel member.

* * * * *